(12) United States Patent
Kelly et al.

US009173979B2

(10) Patent No.: US 9,173,979 B2
(45) Date of Patent: Nov. 3, 2015

(54) BIOABSORBABLE POLYMERIC COMPOSITIONS, PROCESSING METHODS, AND MEDICAL DEVICES THEREFROM

(71) Applicant: Ethicon, Inc., Somerville, NJ (US)

(72) Inventors: Brian M. Kelly, Ringoes, NJ (US); Dennis D. Jamiolkowski, Long Valley, NJ (US); Christopher DeFelice, Hoboken, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 14/084,932

(22) Filed: Nov. 20, 2013

(65) Prior Publication Data

US 2014/0073705 A1 Mar. 13, 2014

Related U.S. Application Data

(62) Division of application No. 12/887,995, filed on Sep. 22, 2010.

(51) Int. Cl.
| | |
|---|---|
| *A61K 47/34* | (2006.01) |
| *A61F 2/00* | (2006.01) |
| *A61F 2/82* | (2013.01) |
| *A61B 17/00* | (2006.01) |
| *A61B 17/04* | (2006.01) |
| *A61B 17/08* | (2006.01) |
| *A61B 17/64* | (2006.01) |
| *A61B 17/84* | (2006.01) |
| *A61B 17/86* | (2006.01) |
| *C08L 67/00* | (2006.01) |
| *A61L 31/04* | (2006.01) |
| *A61B 17/064* | (2006.01) |
| *C08L 67/04* | (2006.01) |
| *A61L 31/14* | (2006.01) |
| *A61L 31/16* | (2006.01) |

(52) U.S. Cl.
CPC .............. *A61L 31/041* (2013.01); *A61B 17/064* (2013.01); *A61L 31/148* (2013.01); *A61L 31/16* (2013.01); *C08L 67/04* (2013.01); *A61B 17/0401* (2013.01); *A61B 2017/00004* (2013.01); *A61B 2017/00526* (2013.01); *A61B 2017/0647* (2013.01); *A61L 2300/404* (2013.01); *A61L 2300/442* (2013.01)

(58) Field of Classification Search
None
See application file for complete search history.

(56) References Cited

U.S. PATENT DOCUMENTS

| | | | |
|---|---|---|---|
| 4,643,191 A * | 2/1987 | Bezwada et al. | 606/230 |
| 4,646,741 A | 3/1987 | Smith | |
| 4,741,337 A | 5/1988 | Smith et al. | |
| 4,889,119 A | 12/1989 | Jamiolkowski et al. | |
| 5,320,624 A | 6/1994 | Kaplan et al. | |
| 5,475,063 A | 12/1995 | Kaplan et al. | |
| 5,641,501 A | 6/1997 | Cooper et al. | |
| 5,697,976 A | 12/1997 | Chesterfield et al. | |
| 5,705,181 A | 1/1998 | Cooper et al. | |
| 5,834,582 A | 11/1998 | Sinclair et al. | |
| 5,883,199 A | 3/1999 | McCarthy et al. | |
| 5,902,319 A | 5/1999 | Daley | |
| 5,997,568 A | 12/1999 | Liu | |
| 6,090,131 A | 7/2000 | Daley | |
| 6,177,094 B1 | 1/2001 | Jiang | |
| 6,228,954 B1 | 5/2001 | Kaplan et al. | |
| 6,332,884 B1 | 12/2001 | Cooper | |
| 6,338,739 B1 | 1/2002 | Datta et al. | |
| 6,423,092 B2 | 7/2002 | Datta et al. | |
| 6,494,908 B1 | 12/2002 | Huxel et al. | |
| 6,495,631 B1 | 12/2002 | Randall et al. | |
| 6,537,312 B2 | 3/2003 | Datta et al. | |
| 6,583,232 B1 | 6/2003 | Brown | |
| 6,607,548 B2 | 8/2003 | Pohjonen | |
| 6,943,214 B2 | 9/2005 | Flexman | |
| 6,981,987 B2 | 1/2006 | Huxel et al. | |
| 7,122,037 B2 | 10/2006 | Happonen et al. | |
| 7,138,441 B1 | 11/2006 | Zhang | |
| 7,163,562 B2 | 1/2007 | Datta et al. | |
| 7,166,134 B2 | 1/2007 | Datta et al. | |
| 7,169,187 B2 | 1/2007 | Datta et al. | |
| 7,282,216 B2 | 10/2007 | Costantino et al. | |
| 7,326,426 B2 | 2/2008 | Nathan et al. | |
| 7,354,973 B2 | 4/2008 | Flexman | |
| 7,381,772 B2 | 6/2008 | Flexman et al. | |
| 2002/0002399 A1 | 1/2002 | Huxel et al. | |
| 2002/0019661 A1 | 2/2002 | Datta et al. | |
| 2002/0106406 A1 | 8/2002 | McHugh et al. | |
| 2002/0143388 A1 | 10/2002 | Datta et al. | |
| 2002/0173595 A1 | 11/2002 | Pohjonen et al. | |
| 2003/0045924 A1 | 3/2003 | Datta et al. | |
| 2003/0133980 A1 | 7/2003 | Costantino et al. | |

(Continued)

OTHER PUBLICATIONS

"Poly(*para*-dioxanone) and Poly(l-lactic acid) Blends: Thermal, Mechanical, and Morphological Properties", A. P. T. Pezzin, G. O. R. Alberda van Ekenstein, C. A. C. Zavaglia, G. ten Brinke, and E. A. R. Duck, Journal of Applied Polymer Science, vol. 88, 2744-2755 (2003).

"Miscibility and Hydrolytic Degradation of Bioreabsorbable Blends of Poly(*p*-Dioxanone) and Poly(L-Lactic Acid) Prepared by Fusion" A. P. T. Pezzin, and E. A. R. Duek, Journal of Applied Polymer Science, Vol, 1899-1912 (2006).

(Continued)

*Primary Examiner* — Robert A Wax
*Assistant Examiner* — Jessica Worsham
(74) *Attorney, Agent, or Firm* — E. Richard Skula

(57) ABSTRACT

Novel bioabsorbable polymeric blends are disclosed. The blends have a first component that is a polylactide polymer or a copolymer of lactide and glycolide and a second component that is poly(p-dioxanone) polymer. The novel polymeric blends provide medical devices having dimensional stability. Also disclosed are novel bioabsorbable medical devices made from these novel polymer blends, as well as novel methods of manufacture.

33 Claims, 6 Drawing Sheets

(56) References Cited

U.S. PATENT DOCUMENTS

| | | |
|---|---|---|
| 2003/0144730 A1 | 7/2003 | Datta et al. |
| 2005/0131120 A1 | 6/2005 | Flexman |
| 2006/0173133 A1 | 8/2006 | Flexman et al. |
| 2006/0188545 A1* | 8/2006 | Hadba .................... 424/426 |
| 2007/0050018 A1 | 3/2007 | Wainwright |
| 2007/0106371 A1 | 5/2007 | Datta et al. |
| 2007/0149640 A1 | 6/2007 | Andjelic et al. |
| 2007/0200268 A1 | 8/2007 | Dave |
| 2007/0200271 A1 | 8/2007 | Dave |
| 2007/0202046 A1 | 8/2007 | Dave |
| 2007/0202146 A1 | 8/2007 | Burgermeister et al. |
| 2007/0202150 A1 | 8/2007 | Dave |
| 2007/0203569 A1 | 8/2007 | Burgermeister et al. |
| 2007/0213466 A1 | 9/2007 | Uradnisheck |
| 2007/0276388 A1 | 11/2007 | Robertson et al. |
| 2008/0071008 A1 | 3/2008 | Smillie et al. |
| 2008/0071018 A1 | 3/2008 | Smillie et al. |
| 2008/0118546 A1 | 5/2008 | Thatcher et al. |
| 2009/0005514 A1 | 1/2009 | Uradnisheck et al. |
| 2009/0118241 A1 | 5/2009 | Andjelic et al. |

OTHER PUBLICATIONS

"Biodegradable Polyester Blends for Biomedical Application" Llanlal Zhanc, Chencdong Xionc, and Xianmo Denc Journal of Applied Polymer Science, vol. 56, 103-112 (1995).

"Miscibility, morphology and thermal properties of poly(para-dioxanone)/poly(D,L-lactide) blends" Wei Bai, Zhi-ping Zhang, Qing Li, Dong-Liang Chen, He-Chun Chen, Polym Int 2009; 58: 183-189.

"Effect of PEG on the crystallization of PPDO/PEG blends" Li Zheng, Yu-Zhong Wang, Ke-Ke Yang, Xiu-Li Wang, Si-Chong Chen, Jun Li, European Polymer Journal 41 (2005) 1243-1250.

"In vitro hydrolytic degradation of poly(para-dioxanone)/poly(d,l-lactide) blends", Wei Bai, Li-Fang Zhang, Qing Li, Dong-Liang Chen, Cheng-Dong Xiong Materials Chemistry and Physics 122 (2010) 79-86.

* cited by examiner

BIOABSORBABLE POLYMERIC COMPOSITIONS, PROCESSING METHODS, AND MEDICAL DEVICES THEREFROM

CROSS REFERENCE TO RELATED APPLICATIONS

This application is a divisional application of pending U.S. application Ser. No. 12/887,995 filed Sep. 22, 2010, the entire disclosures of which are hereby incorporated in their entirety.

FIELD OF THE INVENTION

The field of art to which this invention relates is bioabsorbable polymers, in particular, bioabsorbable polymer blends useful for manufacturing medical devices.

BACKGROUND OF THE INVENTION

Bioabsorbable polymers and medical devices made from such polymers are known in the art. Conventional bioabsorbable polymers include polylactic acid, poly(p-dioxanone), polyglycolic acid, copolymers of lactide, glycolide, p-dioxanone, trimethylene carbonate, ε-caprolactone, in various combinations, etc. The bioabsorbable polymers are designed to have a chemistry such that the polymers breakdown in vivo and are either metabolized or otherwise broken down, for example by hydrolysis, and excreted from the patient's body. The advantages of utilizing implantable medical devices made from bioabsorbable polymers are numerous and include, for example, eliminating the need for additional surgeries to remove an implant after it serves its function. Ideally when a "temporary presence" of the implant is desired, support can be provided until the tissue heals.

The bioabsorbable polymers used to manufacture medical devices have been on occasion polymeric blends of absorbable polymers and copolymers engineered to provide specific characteristics and properties to the manufactured medical device, including bioabsorption rates, breaking strength retention, and dimensional stability, etc.

There are many conventional processes used to manufacture medical devices from bioabsorbable polymers and polymer blends. The processes include injection molding, solvent casting, extrusion, machining, cutting and various combinations and equivalents. A particularly useful and common manufacturing method is thermal forming using conventional injection molding processes. It is known in this art that manufacturing processes such as thermal injection molding may result in molded parts that have inferior properties, especially, for example, unacceptable dimensional stability, mechanical properties, and retention of mechanical properties with time post-implantation. There are a number of reasons for diminished dimensional stability. They include the presence of residual stresses induced during the manufacturing process. Another reason is if at least one of the polymeric components possesses too low a glass transition temperature, especially if the polymeric component does not easily crystallize after molding.

Therefore, there is a need in this art for novel bioabsorbable polymer blends that can be used in thermal injection molding processes, and other conventional processes, to manufacture bioabsorbable medical devices having superior breaking strength retention, excellent bioabsorption, superior mechanical properties such as stiffness and strength, manufacturability, and superior dimensional stability.

It is known when using thermal injection molding processes that process conditions and design elements that reduce shear stress during cavity filling will typically help to reduce flow-induced residual stress. Likewise, those conditions that promote sufficient packing and uniform mold cooling will also typically tend to reduce thermally-induced residual stress. It is often very difficult, if not nearly impossible, to completely eliminate residual stress in injection molded parts. Approaches that have been employed include: (1) attempting to crystallize the part while still in the mold to increase the mechanical rigidity to resist distortion; and, (2) employing resins having a high glass transition temperature ($T_g$).

This later case describes the situation wherein chain mobility is only reached at much higher temperatures, thus protecting the part at the moderate temperatures that the part might be expected to endure during ethylene oxide (EO) sterilization, shipping, and storage. Materials possessing high glass transition temperatures may not necessarily possess other characteristics that are desirable such as absorbability. Residual stresses are believed to be the main cause of part shrinkage and warpage. Parts may warp or distort dimensionally upon ejection from the mold during the injection molding cycle, or upon exposure to elevated temperatures, encountered during normal storage or shipping of the product.

There have been attempts in the prior art to address the problem of lack of dimensional stability in medical devices thermally formed from melt blended bioabsorbable polymers. Smith, U.S. Pat. No. 4,646,741, discloses a melt blend of a lactide/glycolide copolymer and poly(p-dioxanone) used to make surgical clips and two-piece staples. The melt blends of Smith provide molded articles possessing dimensional stability; Smith requires that the amount of poly(p-dioxanone) in the blend is greater than 25 weight percent and teaches away from lower amounts. The polymer blends of Smith have disadvantages associated with their use to manufacture medical devices, including: limited stiffness or Young's modulus, shorter retention of mechanical properties upon implantation, greater sensitivity to moisture limiting the allowable open storage time during manufacture, and, although difficult to quantify, more difficult thermal processing.

As mentioned previously, residual stresses are believed to be the main cause of part shrinkage and warpage. It is known that flow-induced residual stresses may have an effect upon a thermally molded polymeric medical device. Unstressed, long-chain polymer molecules tend to conform to a random-coil state of equilibrium at temperatures higher than the melt temperature (i.e., in a molten state). During thermal processing (e.g. injection molding), the molecules orient in the direction of flow, as the polymer is sheared and elongated. Solidification usually occurs before the polymer molecules are fully relaxed to their state of equilibrium and some molecular orientation is then locked within the molded part. This type of frozen-in, stressed state is often referred to as flow-induced residual stress. Anisotropic, non-uniform shrinkage and mechanical properties in the directions parallel and perpendicular to the direction of flow are introduced because of the stretched molecular structure.

Cooling can also result in residual stresses. For example, variation in the cooling rate from the mold wall to its center can cause thermally-induced residual stress. Furthermore, asymmetrical thermally-induced residual stress can occur if the cooling rate of the two surfaces is unbalanced. Such unbalanced cooling will result in an asymmetric tension-compression pattern across the part, causing a bending moment that tends to cause part warpage. Consequently, parts with non-uniform thickness or poorly cooled areas are prone to unbalanced cooling, and thus to residual thermal stresses.

For moderately complex parts, the thermally-induced residual stress distribution is further complicated by non-uniform wall thickness, mold cooling, and mold constraints.

It should be noted that a common, conventional method of sterilization is exposure to ethylene oxide gas in a sterilization process cycle. Absorbable polymeric devices are frequently sterilized by exposure to ethylene oxide (EO) gas. EO can act as a plasticizer of lactide-glycolide copolymers, and can lower the $T_g$ slightly; this may result in 'shrinkage' and/or 'warpage' of an injection-molded part, especially when exposed to temperatures higher than the Tg. This adds additional processing and handling challenges when using lactide-glycolide polymeric materials for absorbable medical devices. It should be noted that the EO sterilization process not only exposes the part to EO gas, it also exposes the part to elevated temperatures. This usually requires treatment at slightly elevated temperatures. Because EO can act as a plasticizer of synthetic absorbable polyesters, the problems of shrinkage and warpage and general dimensional instability are often exacerbated.

There are a number of processing methods conventionally used to reduce or eliminate shear stresses during processing. Process conditions and design elements that reduce shear stress during cavity filling will help to reduce flow-induced residual stress. Polymeric parts are often heat treated (thermally annealed) to alter their performance characteristics. The reason for the heat treatment processing is to mature the morphological development, for example crystallization and/or stress relaxation. If done successfully, the resulting part may exhibit better dimensional stability and may exhibit better mechanical strength.

Injection molded parts ejected from the injection molding machine that are not already distorted, can be cooled/quenched to room temperature and may appear to be dimensionally sound. Stresses, however, are usually still present and can drive distortion any time the polymer chains are allowed to mobilize. As previously described, this can happen with an increase in temperature or exposure to a plasticizer such as EO gas. In order to overcome this potential driving force for dimensional distortion, a number of strategies have been taken; these include (thermal) annealing.

If the part can be dimensionally constrained, thermal annealing can be employed towards two goals: one is to attempt to reduce the amount of molecular orientation in the polymer chains, also known as stress reduction; and, another is to increase the crystallinity in the part to increase the mechanical rigidity to resist distortion.

With some polymers that readily crystallize, one might be able to crystallize the part while it is still in the mold, but this is an unusual situation. Here the mold cavity not only acts to define the shape of the part, it can act to restrain the shape of the part during the crystallization process. With more-difficult-to-crystallize polymers, the cycle time becomes prohibitively long, and the injection molding process becomes impractical. Thus, the part needs to be ejected from the mold before complete polymer morphology development takes place.

Injection molded parts prepared from semi-crystalline polymers can often be annealed by thermal treatment to increase crystallinity level and complete their polymer morphology development. Often the parts must be physically constrained to avoid the distortion one is attempting to avoid. Once crystallized, the part has increased mechanical rigidity to resist distortion if exposed to normally distorting conditions. Providing suitable physical constraint is often difficult, as it is often labor intensive and economically taxing.

Annealing the ejected part without need for physical constraint is preferred; however what often happens is that the part distorts during the annealing process rendering the part unacceptable for many needs.

It is known in the industry to anneal parts to reduce molded-in-stresses by thermal relaxation. The time and temperature required to relieve stress varies but must often be done below the $T_g$ to avoid gross distortion. Even then the results can vary greatly. It is more difficult to reduce stress levels, without causing distortion, in higher molecular weight resins. It would be relatively easy to reduce molded-in-stresses by thermal relaxation in low molecular weight, high flow, polyesters, as compared to higher molecular weight polyesters.

Regarding the molecular weight of the polymer blend, higher molecular weight usually develops higher stress levels and requires longer times/higher temperatures for stress relaxation. Although this is the case, higher molecular weight is often needed to achieve high mechanical properties and biological performance. This situation often presents a problem for the device manufacturer.

In order to impart more crystallinity to increase mechanical rigidity to better resist distortion, or to reduce molecular orientation in order to lower the driving force for distortion, the parts would ideally be processed by thermal treatment (annealing) at a temperature which does not cause distortion. Unfortunately, due to the nature of the synthetic absorbable polyesters commonly employed, this treatment often needs to be above their glass transition temperature where distortion is nearly impossible to avoid.

Consider for example, polylactide homopolymeric or poly(lactide-co-glycolide) copolymeric devices. The stressed polymer chains of these injection-molded parts will tend to relax and return to their natural state ("random three-dimensional coils") when heated to or above their glass transition temperatures. This will be observed as warpage, shrinkage or general dimensional deformation. It is a general practice in the industry when producing molded polylactide-based parts, not to anneal them because of this potential deformation. These as-molded polylactide parts are of very low crystallinity, if not outright amorphous or non-crystalline, and will then tend to deform if exposed to temperatures at or above their respective glass transition temperatures. It would be advantageous to be able to anneal such parts to induce crystallinity so that they may develop the high rigidity to remain dimensionally stable under conditions normally encountered during EO sterilization, shipping, and storage.

There are medical applications that require the medical device to display sufficient column strength such as in the case of an implantable staple or a tack. Clearly, for a device having such a requirement with a smaller cross-sectional area, the polymer from which it was formed must be inherently stiff if the tack is to function properly for the intended application.

To achieve higher stiffness in a melt blend of a lactide/glycolide copolymer and poly(p-dioxanone), one needs to minimize the amount of poly(p-dioxanone). Contrary to what Smith teaches, it has been found that dimensional stability can be achieved in parts molded from a blend of a lactide-rich copolymer and poly(p-dioxanone), in which the levels of poly(p-dioxanone) are lower than 25 weight percent. The addition of the poly(p-dioxanone), even at these low levels, enhances the ability to achieve dimensional stability in the final part.

Even though such polymer blends are known, there is a continuing need in this art for novel absorbable polymeric materials that provide a medical device with improved characteristics including stiffness, retained strength in vivo (in situ), dimensional stability, absorbability in vivo, and manufacturability, along with a need for novel medical devices made from such polymeric materials, and novel methods of manufacturing medical devices from such polymeric materials.

SUMMARY OF THE INVENTION

It is an object of the present invention to provide novel bioabsorbable polymer blends that can be used in manufacturing processes to produce novel absorbable medical devices and medical device components by melt processes, such as injection molding, and by other processes, wherein the devices or components have superior mechanical properties (such as high stiffness and column strength), superior breaking strength retention, acceptable bioabsorption rates, and superior dimensional stability.

Accordingly, a novel bioabsorbable polymer blend composition is disclosed. The polymer blend has a first bioabsorbable polymer and a second bioabsorbable polymer. The first polymer contains about 76 weight percent to about 92 weight percent of a lactide-rich polymer containing about 100 mol percent to about 70 mol percent of polymerized lactide, and about 0 mol percent to about 30 mol percent of polymerized glycolide. The second polymer is poly(p-dioxanone). The maximum weight percent of poly(p-dioxanone) in the blend is about 24 weight percent and the minimum weight percent of poly(p-dioxanone) in the blend depends upon the molar amount of polymerized lactide in the lactide-rich polymer, and is calculated by the expression:

$$\text{Weight Percent Poly(p-dioxanone)} = (215.6212/\text{Mol Percent Polymerized Lactide})^{2.7027}$$

The polymer blend provides dimensional stability to a manufactured article.

Another aspect of the present invention is a thermally processed bioabsorbable polymer blend composition. The polymer blend has a first bioabsorbable polymer and a second bioabsorbable polymer. The first polymer contains about 76 weight percent to about 92 weight percent of a lactide-rich polymer containing about 100 mol percent to about 70 mol percent of polymerized lactide and about 0 mol percent to about 30 mol percent of polymerized glycolide. The second polymer is poly(p-dioxanone). The maximum weight percent of poly(p-dioxanone) in the blend is about 24 weight percent and the minimum weight percent of poly(p-dioxanone) in the blend depends upon the molar amount of polymerized lactide in the lactide-rich polymer and is calculated by the expression:

$$\text{Weight Percent Poly(p-dioxanone)} = (215.6212/\text{Mol Percent Polymerized Lactide})^{2.7027}$$

The thermally processed polymer blend provides dimensional stability to a manufactured article.

Yet another aspect of the present invention is a novel bioabsorbable medical device. The medical device has a structure. The medical device comprises a bioabsorbable polymer blend of a first bioabsorbable polymer and a second bioabsorbable polymer. The first polymer contains about 76 weight percent to about 92 weight percent of a lactide-rich polymer containing about 100 mol percent to about 70 mol percent polymerized lactide and about 0 mol percent to about 30 mol percent polymerized glycolide. The second polymer is poly(p-dioxanone). The maximum weight percent of poly(p-dioxanone) in the blend is about 24 weight percent and the minimum weight percent of poly(p-dioxanone) in the blend depends upon the molar amount of polymerized lactide in the lactide-rich polymer and is calculated by the expression:

$$\text{Weight Percent Poly(p-dioxanone)} = (215.6212/\text{Mol Percent Polymerized Lactide})^{2.7027}$$

The polymer blend provides dimensional stability to the medical device.

Still yet another aspect of the present invention is a method of manufacturing a medical device. The method includes the steps of processing a bioabsorbable polymer blend. The polymer blend has a first bioabsorbable polymer and a second bioabsorbable polymer. The first polymer contains about 76 weight percent to about 92 weight percent of a lactide-rich polymer containing about 100 mol percent to about 70 mol percent of polymerized lactide and about 0 mol percent to about 30 mol percent of polymerized glycolide. The second polymer is poly(p-dioxanone). The maximum weight percent of poly(p-dioxanone) in the blend is about 24 weight percent and the minimum weight percent of poly(p-dioxanone) in the blend depends upon the molar amount of polymerized lactide in the lactide-rich polymer and is calculated by the expression:

$$\text{Weight Percent Poly(p-dioxanone)} = (215.6212/\text{Mol Percent Polymerized Lactide})^{2.7027}$$

A bioabsorbable medical device is formed from the polymer blend. The polymer blend provides dimensional stability to the formed medical device.

Further aspects of the present invention include the above-described medical device and method, wherein the polymer blend is thermally processed.

These and other aspects and advantages of the present invention will become more apparent from the following description and accompanying drawings.

DETAILED DESCRIPTION OF THE INVENTION

Figure 1:
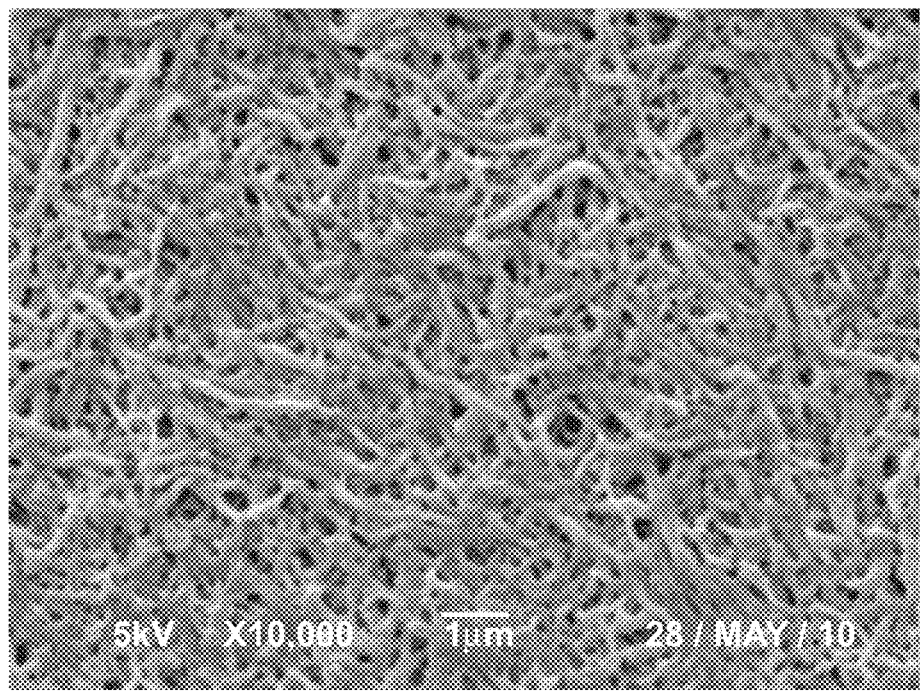
FIG. 1 is a SEM photomicrograph of the collected poly(p-dioxanone) structures of the injection molded articles from the polymer blend of 20 weight percent poly(p-dioxanone) and 80 weight percent poly(lactide-co-glycolide), wherein the poly(lactide-co-lactide) is 85 mol percent polymerized lactide and 15 mol percent polymerized glycolide.

The novel polymer blends of the present invention are made from bioabsorbable polyester polymers and copolymers. Preferably, one of the blend components is either poly(L(−)-lactide), or a lactide-rich lactide/glycolide copolymer. Another blend component is the bioabsorbable polymer poly(p-dioxanone).

The poly(L(−)-lactide), or a lactide-rich lactide/glycolide copolymer will be manufactured in a conventional manner. A preferred manufacturing method is as follows: the lactone monomers are charged along with an alcohol initiator, a suitable catalyst, and dye if desired, into a stirred pot reactor. After purging to remove oxygen, under a nitrogen atmosphere the reactants are heated with agitation to conduct a ring opening polymerization. After a suitable time the formed resin is discharged and sized appropriately. The resin particles are subjected to a devolitalization process and are subsequently stored under vacuum. The mol percent of polymerized lactide and polymerized glycolide in the lactide-rich polymer useful in the novel blends of the present invention may be varied to provide desired characteristics. Typically, the mol percent of polymerized lactide in the lactide-rich polymer will be about 70 percent to about 100 percent, more typically about 80 percent to about 90 percent, and preferably about 83 percent to about 87 percent. When the polymerized lactide in the lactide-rich polymer is 100 percent, the polymer is polylactide; poly(L(−)-lactide) is preferred for some surgical applications. Typically, the mol percent of polymerized glycolide in the lactide-rich polymer will be about 0 percent to about 30 percent, more typically about 10 percent to about 20 percent, and preferably about 13 percent to about 17 percent.

The poly(L(−)-lactide) homopolymer, or a lactide-rich lactide/glycolide copolymer is characterized by chemical analysis. These characteristics include, but are not limited to, an inherent viscosity range from about 0.80 to about 2.25 dL/g, as measured in hexafluoroisopropanol at 25° C. and at a concentration of 0.1 g/dL. Gel permeation chromatography analysis showed a weight average molecular weight range from approximately 35,000 to 120,000 Daltons. It is to be understood that higher molecular weight resins can be employed provided the processing equipment used to form the blend, and to form the medical device, is capable of handling the melt viscosities inherent to these higher molecular weights and may be desirable for certain applications. For example, in some applications, a resin with an inherent viscosity of 2.5 dL/g may be needed to produce medical devices requiring certain characteristics, such as higher strength. Differential scanning calorimetry showed a glass transition temperature range from 20 to 65° C. and a melting transition from approximately 120 to 180° C. Nuclear magnetic resonance analysis confirmed that the copolymeric resin is a random copolymer of L(−)-lactide and glycolide. X-ray diffraction analysis showed a crystallinity level of approximately 20 to 45 percent.

It is to be understood that the polylactide homopolymer blend component, or a lactide-rich lactide/glycolide copolymer blend component can be based on the lactide monomer of LL configuration, that is, L(−)-lactide. However, other stereochemical isomers can be substituted provided that in the final device, the lactide based polymer component exhibits enough crystallinity to provide dimensional stability. Thus, the homopolymer, poly(D(+)-lactide) based on the DD configuration might be used instead of poly(L(−)-lactide). A lactide/glycolide copolymer component might be based entirely on the DD-isomer, or have mixtures of the DD-isomer and the LL-isomer, provided the crystallinity requirement in the final device is met. Meso-lactide, the DL-isomer might also be used in small proportions, again provided the crystallinity requirement in the final device is met.

The poly(p-dioxanone) polymer useful in the novel polymer blends of the present invention is manufactured in a conventional manner. A preferred method of manufacturing such polymer is as follows: the lactone monomer is charged along with an alcohol initiator, a suitable catalyst, and dye if desired, into a stirred pot reactor. The dye should be one acceptable for clinical use; these include D&C Violet No. 2 and D&C Blue No. 6. After purging to remove oxygen, the reactants are heated under a nitrogen atmosphere with agitation to conduct a ring opening polymerization. After a suitable time, the formed resin is discharged into appropriate containers, and further polymerized under conditions known as "solid state" polymerization. An alternative method may include polymerization in the melt. After this reaction period is complete, the polymer resin is sized appropriately. The resin particles are subjected to a devolitalization process to remove unreacted monomer and are subsequently stored under vacuum. The polydioxanone polymers useful in the blends of the present invention will have an inherent viscosity of at least about 0.80 dL/g as measured at 25° C. and at a concentration of 0.1 g/dL. The polydioxanone polymers particularly useful in the blends of the present invention will have the following characteristics: These characteristics shall include, but are not limited to: an inherent viscosity range from about 0.80 to about 2.30 dL/g, as measured in hexafluoroisopropanol at 25° C. and at a concentration of 0.1 g/dL. Gel permeation chromatography analysis showed a weight average molecular weight range from approximately 35,000 to 120,000 Daltons. It is to be understood that higher molecular weight resins can be employed provided the processing equipment used to form the blend, and to form the medical device, is capable of handling the melt viscosities inherent to these higher molecular weights and may be desirable for certain applications. For example, in some applications, a resin with an inherent viscosity of 2.5 dL/g may be needed to produce medical devices requiring certain characteristics, such as higher strength. Differential scanning calorimetry showed a glass transition temperature range from −15 to −8° C. and a melting transition from approximately 100 to 107° C. Nuclear magnetic resonance analysis confirmed that the resin is a homopolymer of poly(p-dioxanone), with a composition of approximately 98 percent polymerized p-dioxanone, and approximately 0 to 2 percent p-dioxanone monomer, as measured on a molar basis. X-ray diffraction analysis typically showed a crystallinity level of approximately 25 to 40 percent, although levels of 55 percent or higher have been observed.

The novel polymer blends of the present invention having improved dimensional stability will typically contain a first bioabsorbable polymer and a second bioabsorbable polymer, the first polymer containing about 76 weight percent to about 92 weight percent of a lactide-rich polymer containing about 100 mol percent to about 70 mol percent polymerized lactide and about 0 mol percent to about 30 mol percent polymerized glycolide, and the second polymer containing poly(p-dioxanone), wherein the maximum weight percent of poly(p-dioxanone) in the blend is about 24 and the minimum weight percent of poly(p-dioxanone) in the blend depends upon the molar amount of polymerized lactide in the lactide-rich polymer and is calculated by the expression:

$$\text{Weight Percent Poly(p-dioxanone)} = (215.6212/\text{Mol Percent Polymerized Lactide})^{2.7027}$$

To be clear, the novel polymer blends of the present invention are typically a blend of a lactide-rich lactide/glycolide copolymer or a polylactide homopolymer, and poly(p-dioxanone). For example, the lactide/glycolide copolymer can be poly(L(−)-lactide-co-glycolide) having a composition of 85 mol percent polymerized lactide and 15 mol percent polymerized glycolide. The maximum weight percent of poly(p-dioxanone) in the blend is about 24 and one can calculate the minimum weight percent of poly(p-dioxanone) in the blend depending upon the molar amount of polymerized lactide in the lactide/glycolide copolymer, using the above equation. Thus for the case of an 85/15 (mol basis) lactide/glycolide copolymer:

$$\text{Minimum Weight Percent Poly(p-dioxanone)} = (215.6212/\text{Mol Percent Polymerized Lactide})^{2.7027} = (215.6212/85)^{2.7027} = 12.4 \text{ Weight Percent Poly(p-dioxanone)}$$

Thus for the novel polymer blends of the present invention employing an 85/15 (mol basis) lactide/glycolide copolymer, the poly(p-dioxanone) weight percent would range between about 12.4 and about 24.

The novel polymer blends of the present invention will more typically contain about 76 weight percent to about 84 weight percent of the lactide-rich polymer, and about 16 weight percent to about 24 weight percent of the poly(p-dioxanone), wherein the lactide-rich polymer contains about 80 mol percent to about 90 mol percent of polymerized lactide and from about 10 mol percent to about 20 mol percent of polymerized glycolide.

The novel polymer blends of the present invention will preferably contain about 78 weight percent to about 82 weight percent of the lactide-rich polymer, and about 18 weight percent to about 22 weight percent of the poly(p-dioxanone), wherein the lactide-rich polymer contains about 83 mol percent to about 87 mol percent of polymerized lactide and from about 13 mol percent to about 17 mol percent of polymerized glycolide.

The blends of the present invention showed a crystallinity level of at least about 15 percent, typically greater than about 25 percent, and more preferably, greater than about 35 percent, as measured by x-ray diffraction.

The novel polymer blends of the present invention can be manufactured from the individual components in a variety of conventional manners using conventional processing equipment. Examples of manufacturing processes include chemical reactions of the ring-opening and polycondensation type, devolitilization and resin drying, dry blending in a tumble dryer, solution blending, extrusion melt-blending, injection molding, thermal annealing, and ethylene oxide sterilization processes. An alternate to dry blending with subsequent melt blending of the mixture could include the use of two or more feeders, preferably loss-in-weight feeders, that supply the components to be blended to an extruder; the extruder can be of the single screw or twin screw variety. Alternately, multiple extruders can be used to feed melts of the blend components, such as in co-extrusion.

The blends of the present invention may be made by thermal processes. Examples of thermal processes to produce the polymer blends of the present invention would be melt blending in an extruder which can include twin screw blending or single screw extrusion, co-extrusion, twin screw blending with simultaneous vented-screw vacuum devolatilization, vacuum tumble drying with thermal devolitilization, monomer removal by solvent extraction at elevated temperature, and resin annealing.

The polymer components, as well as blends of the subject invention can be sized by conventional means such as pelletization, granulation, and grinding.

A further embodiment of the present invention would be feeding appropriately sized particles of the blend components directly to the hopper of the injection molding machine. It would be obvious to one skilled in the art to apply this technique to other processing methodologies, such as, but not limited to, film or fiber extrusion. Limiting the thermal history of the polymer blend components is advantageous in that it avoids the possibility of premature degradation. Additional methods of thermal processing can include a process selected from the group consisting of injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion. As noted earlier, appropriately sized particles of the blend components can be blended in the melt using these thermal processing means.

Although not wishing to be held to scientific theory, it is believed that the morphological development in the final part is greatly influenced by the device forming process, such as injection molding. Thus the melt blended resin may have a morphology with a very low aspect ratio for the minor phase, polyp-dioxanone). It may not be until the high shear device forming process (e.g., injection molding), that the high aspect ratio of the minor phase is realized.

Other examples of manufacturing process equipment include chemical reactors ranging in size from two-gallon to seventy-five gallon capacity, process devolitilization dryers ranging from one cubic feet to twenty cubic feet, single and twin-screw extruders from about one inch to about three inches in diameter, and injection molders ranging from about seven to about 40 tons in size. A preferred method and associated equipment for manufacturing the polymer blends of the present invention can be found in EXAMPLE 1 through EXAMPLE 6.

If desired, the polymer blends of the present invention may contain other conventional components and agents. The other components, additives or agents will be present to provide additional effects to the polymer blends and medical devices of the present invention including antimicrobial characteristics, controlled drug elution, radio-opacification, and osseointegration.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents include the polychloro phenoxy phenols such as 5-chloro-2-(2,4-dichlorophenoxy) phenol (also known as Triclosan).

Examples of radio-opacification agents include barium sulfate while examples of osseointegration agents include tricalcium phosphate.

The variety of therapeutic agents that can be used in the polymer blends of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligo-nucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Suitable polymers that may be included in the polymer blends of the present invention include: suitable biocompatible, biodegradable polymers which may be synthetic or natural polymers. Suitable synthetic biocompatible, biodegradable polymers include polymers selected from the group consisting of aliphatic polyesters, poly(amino acids), copoly (ether-esters), polyalkylenes oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, polydiglycolates, and combinations thereof. It is to be understood that inclusion of additional suitable polymers is dependent upon obtaining dimensional stability in the fabricated device.

For the purposes of this invention the above optional aliphatic polyesters include, but are not limited to, homopolymers and copolymers of lactide (which include lactic acid, D-, L- and meso lactide), glycolide (including glycolic acid), epsilon-caprolactone, p-dioxanone (1,4-dioxan-2-one), trimethylene carbonate (1,3-dioxan-2-one), alkyl derivatives of trimethylene carbonate, and blends thereof.

Suitable natural polymers include, but are not limited to collagen, elastin, hyaluronic acid, laminin, gelatin, keratin, chondroitin sulfate and decellularized tissue.

Although not preferred, the medical devices of the present invention may contain nonabsorbable polymers in addition to the absorbable polymer blends of the present invention. Examples of such devices may include but are not limited to meshes, sutures, and staples, where the properties of both the absorbable and nonabsorbable polymers are advantageous.

Suitable nonabsorbable polymers include, but are not limited to acrylics; polyamide-imide (PAI); polyaryletherketones (PEEK); polycarbonates; thermoplastic polyolefins such as polyethylene (PE), polypropylene (PP), polymethylpentene (PMP), and polybutene-1 (PB-1); polyolefin elastomers (POE) such as polyisobutylene (PIB), ethylene propylene rubber (EPR); polybutylene terephthalate (PBT); polyethylene terephthalates (PET); polyamides (PA) such as nylon 6 and nylon 66; polyvinylidene fluoride (PVDF); polyvinylidene fluoride-co-hexafluoropropylene (PVDF/HFP); polymethylmethacrylate (PMMA) and combinations thereof and equivalents.

The bioabsorbable medical devices of the present invention that are made from the polymer blends of the present invention include but are not limited to conventional medical devices, especially implantable medical devices, including staples, tacks, clips, sutures, tissue fixation devices, mesh fixation devices, anastomosis devices, suture and bone anchors, tissue and bone screws, bone plates, prostheses, support structures, tissue augmentation devices, tissue ligating devices, patches, substrates, meshes, tissue engineering scaffolds, drug delivery devices, and stents.

Figure 2:
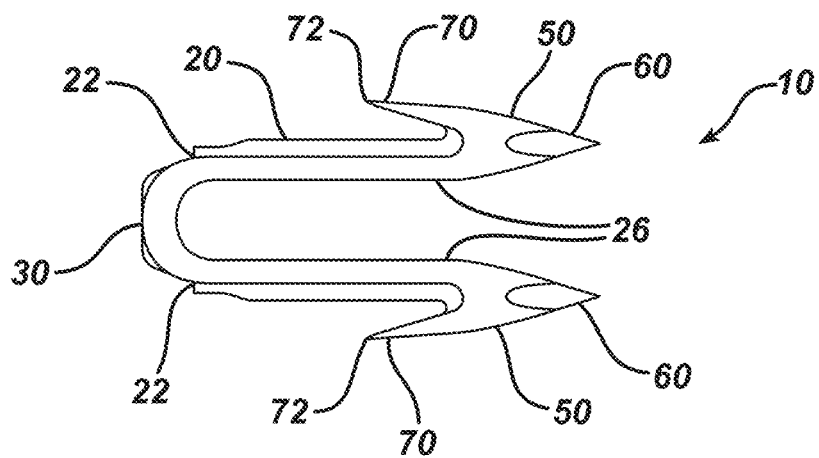
FIG. 2 is a drawing of an implantable staple or tack demonstrating the present invention, and shows a device with a small cross-sectional area.

An example of a medical device that can be molded from the polymer blends of the present invention is a tissue tack 10 as seen in FIG. 2. FIG. 2 is a drawing of an implantable staple or tack demonstrating the present invention, and shows a device with a small cross-sectional area. The material of this device must be inherently stiff if the tack is to function properly for the intended application.

Figure 3:
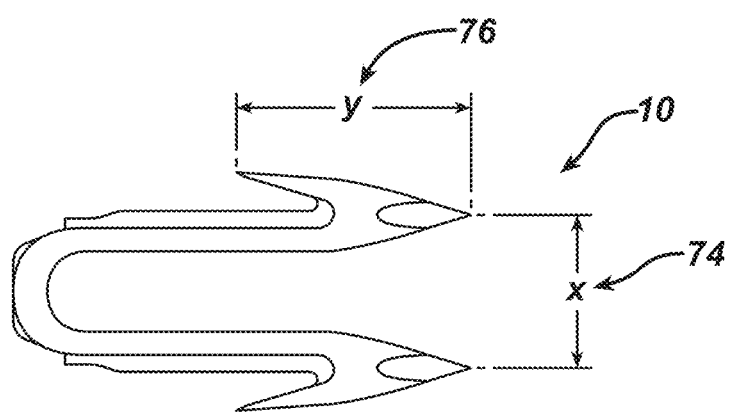
FIG. 3 is a drawing of the device of FIG. 2 showing critical dimensions of said device.

The tack 10 is seen to have two leg members 20 connected by a connecting strap member 30 at their proximal ends 22. The distal ends 26 are seen to have barb members 50 extending distally therefrom. Barb members 50 have distal tissue piercing points 60 and proximal barbs 70 having points 72. Referring to FIG. 3, barb members 50 are seen to have a length 74 shown as dimension Y. The points 60 are seen to be spaced apart by a distance 76 shown as dimension X.

Suitable tacks that can be made from the polymer blends of the present invention are also disclosed and described in commonly-assigned U.S. patent application Ser. Nos. 12/464,143; 12/464,151; 12/464,165; and, 12/464,177, which are incorporated by reference.

The ability of the injection molded articles to develop some level of crystallinity prior to annealing allows the parts to undergo an annealing cycle to further crystallize the poly(lactide-co-glycolide) phase of the blend without unduly warping or shrinking, that is while maintaining dimensional integrity.

Injection molded parts of the blends of the subject invention can advantageously be subjected to an annealing cycle to mature the polymer morphology. This often increases the level of crystallinity in the part. This process helps to ensure that when the part is exposed to moderately elevated temperatures, especially when exposed to ethylene oxide during sterilization, dimensional stability will be acceptable. Although not wanting to be held to scientific theory, it is believed that directly after injection molding, under many processing conditions, the articles are almost completely amorphous, but when stored at room temperature the poly(p-dioxanone) phase in the blend begins to crystallize. Polymeric materials will only crystallize when stored at temperatures above their glass transition temperature. The glass transition temperature of poly(p-dioxanone) is about minus 10° C., allowing the poly(p-dioxanone) to begin crystallizing during storage at room temperature. In some processing conditions, typically at longer holding times in the mold, the poly(p-dioxanone) component can crystallize. The ejected parts then possess a small amount of crystallinity due substantially to this phase.

The ability of the poly(p-dioxanone) phase in the blend to develop some level of crystallinity prior to annealing allows for the crystallization of the poly(lactide-co-glycolide) phase without excessive distortion of the molded article. This is because the formation of an organized, semicrystalline, molecular structure increases the part's resistance to distortion at elevated temperatures. For instance, if an amorphous, 100% poly(lactide-co-glycolide) article were to be annealed, the part would likely warp during the annealing process if there were even moderate stress levels present. The interdispersed, semicrystalline poly(p-dioxanone) in the blend maintains the dimensional stability of the part during exposure to the elevated temperatures needed to crystallize the poly(lactide-co-glycolide) phase of the blend. The end result is a semicrystalline, dimensionally stable, injection molded article.

The medical devices of the present invention can be thermally annealed at a temperature of at least 45 degrees centigrade for at least one minute. More preferably, the medical devices of the present invention are thermally annealed at a temperature of about 60 degrees centigrade for about 8 hours, followed by annealing at a temperature of about 70 degrees centigrade for about 4 hours, followed by annealing at a temperature of about 80 degrees centigrade for about 4 hours.

The medical device of the present invention will exhibit a crystallinity level of at least about 15 percent, typically greater than about 25 percent, and more preferably, greater than about 35 percent, as measured by x-ray diffraction.

To further inhibit warping during the annealing process, the article may also be constrained mechanically by use of an annealing fixture. Speculatively, it may be possible to anneal the part fully confined, or constrained. This would require the equivalent of annealing in the mold. This, of course, is often economically not feasible. However, constraining a limited number of dimensions during annealing may be economically possible. The articles in EXAMPLE 8 were annealed using an annealing fixture that supported the parts from distortion within the horizontal plane of the part. Although this annealing fixture is intended to aid in the resistance of distortion at elevated temperatures during annealing, it will not prevent dimensionally unstable parts from warping.

As the lactide level in the poly(lactide-co-glycolide) portion of the blend decreases, crystallization of the poly(lactide-co-glycolide) phase becomes more difficult. In blends using a poly(lactide-co-glycolide) copolymer less rich in polymerized lactide, an increased weight percent of poly(p-dioxanone) may be required to maintain dimensional stability of the molded article. Such copolymers include 70/30 poly(lactide-co-glycolide).

As noted earlier, the greater the amount of molecular orientation, or stress, present in the formed medical device, the greater will be the driving force to shrink or warp; shrinking and warping is usually viewed as a disadvantageous phenomena.

In the formation of devices using processing means that induce at least a moderate level of molecular orientation, or stress, it would be an advantage to maintain dimensional stability. One such fabrication methodology that usually induces at least a moderate level of stress is injection molding. To be clear, when forcing a molten polymer stream through a pathway that is narrow, and finally into a cavity, one usually encounters high shear rates and high stress levels. When this happens, the molecular chains tend to orient in the direction of the flow, thereby setting up the system for later shrinkage or warpage when subjected to temperatures slightly elevated above the glass transition temperature, particularly during exposure to EO gas while sterilizing.

Evidence of a high shear forming process is the presence of high residual stresses in the part; these can be measured in a variety of ways. One such way is by viewing a part through crossed-polarized films. Other ways of assessing residual stresses utilize Scanning Electron Microscopy (SEM) techniques. The phase architecture of the substantially immiscible polymer blends of lactide/glycolide copolymers and poly(p-dioxanone) further provide evidence of the level of stress that the blend was subjected to during processing. When in high shear situations, usually the minor phase is non-spherical in nature. The minor phase usually distorts to elongated ellipsoids with L/Ds greater than about 3 to worm-like structures having L/D values 50 or greater. The medical devices of the present invention will typically have aspect ratios of the minor phase greater than about 3, more typically greater than about 5, and preferably greater than about 20. Depending on the shear field, one could envision non-circular cross-sections that are more ribbon-like. When the minor phase is substantially spherical in nature, one can conclude that: (1) the level of shear the polymer melt was subjected to was quite low or (2) the processing conditions employed allowed the polymer melt to relax, and the subsequent elongated domains reshaped to much lower L/D structures. In either case, the level of residual stress is expected to be low. A sphere-only minor phase morphology may then be evidence of low residual stress.

Methods to ascertain phase architecture in immiscible polymer blends include phase contrast microscopy (polarized light microscopy); atomic force microscopy (AFM); electron microscopy including scanning, tunneling and transmission electron microscopy(SEM, STM, TEM). Other techniques potentially include high resolution digital-optical microscopy.

Sample preparation may be via cryogenic fracturing or by microtoming techniques including cryogenic microtoming Solvent etching has proven to be a useful sample preparation methodology in a number of systems.

As would be known to one having ordinary skill in the art, in accessing the morphology of the minor phase, it is important to realize that one needs to make measurements on the sample from different angular perspectives. Specifically, in parts having elongated features as might be found in the present article of this invention, an examination looking at only the cross-section may incorrectly indicate that the minor phase is spherical in nature. Only when assessed longitudinally will it be revealed that the minor phase is actually elongated in nature with a high aspect ratio.

The medical devices of the present invention will have an inherent viscosity of at least about 0.8 dL/g as measured in hexafluoroisopropanol at 25 degrees centigrade at a concentration of 0.1 g/dL. Additionally, the inherent viscosity of the lactide-rich polymer will be at least about 0.8 dL/g and the inherent viscosity of the poly(p-dioxanone) will be at least about 0.8 dL/g, both as measured in hexafluoroisopropanol at 25 degrees centigrade at a concentration of 0.1 g/dL.

The medical devices of the present invention will remain dimensionally stable when subjected to immersion in water at an elevated temperature. Preferably they will remain dimensionally stable when subjected to immersion in water at 49 degrees centigrade. Most preferably, they will remain dimensionally stable when subjected to immersion in water at 70 degrees centigrade.

In a preferred embodiment of the invention (EXAMPLE 7), the injection molded part is visible in the surgical field because the polymeric blend has a violet colorant, or dye, interspersed throughout. This dye, D&C Violet #2, is introduced to the blend as part of the poly(p-dioxanone) homopolymer, which comprises from about 7 to about 24 weight percent of the blend. Alternatively, colorant may be introduced to the blend as part of the lactide-based polymer. In yet another variation, the dye may be added at the time the polymer components are blended together, such as during a melt blending or dry blending process. It will be evident to one skilled in the art that the colorants may be added to the polymer compositions of the present invention in a variety of conventional manners in addition to the approaches described above. The colorants may include D&C Violet No. 2 and D&C Blue No. 6, at amounts ranging from about 0.01 weight percent to about 0.3 weight percent of the polymer blend or medical device. For surgical applications where color is not needed or desirable, undyed poly(p-dioxanone) homopolymer is used in the blend, so that the surgical article has no color.

The following examples are illustrative of the principles and practice of the present invention, although not limited thereto.

EXAMPLE 1

Synthesis of Poly(L(−)-Lactide)

Into a suitable 15-gallon stainless steel oil jacketed reactor equipped with agitation, 25.0 kg of L(−)-lactide was added along with 58.77 g of dodecanol and 4.38 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 180° C., with a heat up rate of approximately 60° C. per hour. When the molten mass reached 178° C., the oil temperature was maintained at approximately 180° C. for an additional period of 3 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 80° C. for a period of approximately 16 hours; during this step the nitrogen flow into the oven was maintained to reduce degradation due to moisture.

Once this annealing cycle was completed, the polymer containers were removed from the oven and allowed to cool to room temperature. The crystallized polymer was removed from the containers and placed into a freezer set at approximately −20° C. for a minimum of 24 hours. The polymer was removed from the freezer and placed into a Cumberland granulator fitted with a sizing screen to reduce the polymer granules to approximately 3/16 inches in size. The granules were then sieved to remove any "fines" and weighed. The net weight of the ground polymer was 18.08 kg, which was then placed into a 3 cubic foot Patterson-Kelley tumble dryer.

The dryer was closed and the pressure was reduced to less than 200 mTorr. Once the pressure was below 200 mTorr, dryer rotation was activated at a rotational speed of 5-10 RPM with no heat for 10 hours. After the 10 hour period, the oil temperature was set to 120° C. at a heat up rate of 120° C. per hour. The oil temperature was maintained at approximately 120° C. for a period of 32 hours. At the end of this heating period, the batch was allowed to cool for a period of 4 hours, while maintaining rotation and vacuum. The polymer was discharged from the dryer by pressurizing the vessel with nitrogen, opening the discharge valve, and allowing the polymer granules to descend into waiting vessels for long term storage.

The long term storage vessels were air tight and outfitted with valves allowing for evacuation so that the resin was stored under vacuum. The resin was characterized. It exhibited an inherent viscosity of 1.84 dL/g, as measured in hexafluoroisopropanol at 25° C. and at a concentration of 0.10 g/dL. Gel permeation chromatography analysis showed a weight average molecular weight of approximately 121,000 Daltons. Differential scanning calorimetry revealed a glass transition temperature of 65° C. and a melting transition at 182° C. Nuclear magnetic resonance analysis confirmed that the resin was poly(L(−)-lactide) with a residual monomer content less than 1.0 percent. X-Ray diffraction analysis showed a crystallinity level of approximately 64 percent.

EXAMPLE 2

Synthesis of 85/15 Poly(L(−)-Lactide-Co-Glycolide)

Into a suitable 15-gallon stainless steel oil jacketed reactor equipped with agitation, 43.778 kg of L(−)-lactide and 6.222 kg of glycolide were added along with 121.07 g of dodecanol and 9.02 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 185° C., with a heat up rate of approximately 60° C. per hour, until the molten mass reached 180° C. The oil temperature was maintained at approximately 185° C. for a period of 2.5 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 105° C. for a period of approximately 6 hours; during this step the nitrogen flow into the oven was maintained to reduce degradation due to moisture.

Once this annealing cycle was complete, the polymer containers were removed from the oven and allowed to cool to room temperature. The crystallized polymer was removed from the containers and placed into a freezer set at approximately −20° C. for a minimum of 24 hours. The polymer was removed from the freezer and placed into a Cumberland granulator fitted with a sizing screen to reduce the polymer granules to approximately 3/16 inches in size. The granules were then sieved to remove any "fines" and then weighed. The net weight of the ground polymer was 39.46 kg, which was then placed into a 3 cubic foot Patterson-Kelley tumble dryer.

The dryer was closed and the pressure is reduced to less than 200 mTorr. Once the pressure is below 200 mTorr, tumbler rotation was activated at a rotational speed of 8-15 RPM and the batch was vacuum conditioned for a period of 10 hours. After the 10 hour vacuum conditioning, the oil temperature was set to a temperature of 120° C., for a period of 32 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin is stored under vacuum. The resin was characterized. It exhibited an inherent viscosity of 1.64 dL/g, as measured in hexafluoroisopropanol at 25° C. and at a concentration of 0.10 g/dL. Gel permeation chromatography analysis showed a weight average molecular weight of approximately 96,200 Daltons. Differential scanning calorimetry revealed a glass transition temperature of 56° C. and a melting transition at 154° C. Nuclear magnetic resonance analysis confirmed that the resin was a random copolymer of polymerized L(−)-lactide and glycolide, with a composition of 83.1 percent polymerized L(−)-lactide, 15.2 percent polymerized glycolide, 1.6 percent lactide monomer, and 0.1 percent glycolide monomer, as measured on a molar basis. The total residual monomer content was approximately 1.7 percent. X-ray diffraction analysis showed a crystallinity level of approximately 48 percent.

EXAMPLE 3

Synthesis of 75/25 Poly(L(−)-Lactide-Co-Glycolide)

Into a suitable 15-gallon stainless steel oil-jacketed reactor equipped with agitation, 19.709 kg of L(−)-lactide and 5.291 kg of glycolide were added along with 61.77 g of dodecanol and 4.60 mL of a 0.33M solution of stannous octoate in toluene. The reactor was closed and a purging cycle, along with agitation at a rotational speed of 12 RPM in an upward direction, was initiated. The reactor was evacuated to pressures less than 200 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 130° C. The vessel was held at 130° C. until the monomer was completely melted and the batch temperature reached 110° C. At this point the agitation rotation was switched to the downward direction. When the batch temperature reached 120° C., the agitator speed was reduced to 7.5 RPM, and the vessel was heated using an oil temperature of approximately 185° C., with a heat up rate of approximately 60° C. per hour. Once the molten mass reached 180° C., the oil temperature was maintained at 185° C. for a period of 2.5 hours.

At the end of the reaction period, the agitator speed was reduced to 5 RPM, the oil temperature was increased to 190° C., and the polymer was discharged from the vessel into suitable containers for subsequent annealing. The containers were introduced into a nitrogen annealing oven set at 105° C. for a period of approximately 6 hours; during this step the nitrogen flow into the oven was maintained to reduce degradation due to moisture.

Once this annealing cycle was completed, the polymer containers were removed from the oven and allowed to cool to room temperature. The crystallized polymer was removed from the containers and placed into a freezer set at approximately −20° C. for a minimum of 24 hours. The polymer was removed from the freezer and placed into a Cumberland granulator fitted with a sizing screen to reduce the polymer granules to approximately 3/16 inches in size. The granules were then sieved to remove any "fines" and then weighed. The net weight of the ground polymer was 17.89 kg, which was then placed into a 3 cubic foot Patterson-Kelley tumble dryer.

The dryer was closed and the pressure was reduced to less than 200 mTorr. Once the pressure was below 200 mTorr, tumbler rotation was activated at a rotational speed of 5-15 RPM and the polymer was conditioned for 16 hours under vacuum with no heat. The dryer temperature was then set to 60-65° C. at a heat up rate of 100° C. per hour. The oil temperature was maintained at 60-65° C. for a period of approximately 9 hours. At the end of this heating period, the batch was allowed to cool for a period of at least 4 hours, while maintaining rotation and high vacuum. The polymer was discharged from the dryer by pressurizing the vessel with nitrogen, opening the slide-gate, and allowing the polymer granules to descend into waiting vessels for long term storage.

The long term storage vessels were air tight and outfitted with valves allowing for evacuation so that the resin was stored under vacuum. The resin was characterized. It exhibited an inherent viscosity of 1.56 dL/g, as measured in hexafluoroisopropanol at 25° C. and at a concentration of 0.10 g/dL. Gel permeation chromatography analysis showed a weight average molecular weight of approximately 102,000 Daltons. Differential scanning calorimetry revealed a glass transition temperature of 48° C. and a melting transition at 132° C. Nuclear magnetic resonance analysis confirmed that the resin was a random copolymer of polymerized L(−)-lactide and glycolide, with a composition of 70.1 percent polymerized L(−)-lactide, 25.2 percent polymerized glycolide, 4.5 percent lactide, and 0.2 percent glycolide, as measured on a molar basis. The total residual monomer content was less than 5 percent. X-ray diffraction analysis showed a crystallinity level of approximately 26 percent.

EXAMPLE 4

Synthesis of Poly(p-Dioxanone)

Into a suitable 65 gallon stainless steel oil-jacketed reactor equipped with agitation, 164.211 kg of p-dioxanone monomer (PDO) was added along with 509 grams of dodecanol, 164 grams of D&C Violet #2 Dye, and 100 grams of a 0.33M solution of stannous octoate in toluene. The reactor was closed and a purging cycle, along with agitation at a rotational speed of 12 RPM in an upward direction, was initiated. The reactor was evacuated to pressures less than 500 mTorr followed by the introduction of nitrogen gas. The cycle was repeated several times to ensure a dry atmosphere.

At the end of the final introduction of nitrogen, the pressure was adjusted to be slightly above one atmosphere. The vessel was heated at a rate of 180° C. per hour until the oil temperature reached approximately 100° C. The vessel was held at 100° C. until the batch temperature reached 50° C., at which point the agitator rotation was changed to the downward direction. When the batch temperature reached 90° C., the oil temperature was reset to 95° C. These conditions were maintained, and samples were taken from the vessel to be measured for Brookfield viscosity. When the polymer batch viscosity reached at least 110 centipoise, the batch was ready for discharge. The agitator speed was reduced to 5 RPM, and a pre-heated filter was attached to the vessel discharge port. The polymer was discharged from the vessel into suitable containers, under a nitrogen purge, covered, and transferred into a nitrogen curing oven set at 80° C. A solid state polymerization was initiated for a period of approximately 96 hours; during this step the nitrogen flow into the oven was maintained to minimize degradation due to moisture.

Once the solid state curing cycle was complete, the polymer containers were removed from the oven and allowed to cool to room temperature. The crystallized polymer was removed from the containers, and placed into a freezer set at approximately −20° C. for a minimum of 24 hours. The polymer was removed from the freezer and ground in a Cumberland granulator fitted with a sizing screen to reduce the polymer granules to approximately 3/16 inches in size. The granules were then sieved to remove any "fines" and then placed into a 20 cubic foot Patterson-Kelley tumble dryer.

The dryer was closed and the pressure was reduced to less than 2 mmHg. Once the pressure was below 2 mmHg, dryer rotation was activated at a rotational speed of 6 RPM with no heat for 10 hours. After the 10 hour period, the oil temperature was set to 95° C. at a heat up rate of 120° C. per hour. The oil temperature was maintained at 95° C. for a period of 32 hours. At the end of this heating period, the batch was allowed to cool for a period of at least 4 hours, while maintaining rotation and vacuum. The polymer was discharged from the dryer by pressurizing the vessel with nitrogen, opening the discharge valve, and allowing the polymer granules to descend into waiting vessels for long term storage. The storage vessels were air tight and outfitted with valves allowing for evacuation so that the resin was stored under vacuum.

The resin was characterized. It exhibited an inherent viscosity of 1.99 dL/g, as measured in hexafluoroisopropanol at 25° C. and at a concentration of 0.10 g/dL. Gel permeation chromatography analysis showed a weight average molecular weight of approximately 85,000 Daltons. Differential scanning calorimetry revealed a glass transition temperature of about −15° C. and a melting transition at about 105° C. Nuclear magnetic resonance analysis confirmed that the resin was the homopolymer polyp-dioxanone), with a residual monomer content less than 2 percent. X-ray diffraction analysis showed a crystallinity level of approximately 40 percent. For polymers with a different target molecular weight, the initiator (dodecanol) can be adjusted to target the I.V. required. In addition, if the surgical application does not require an article with color, the addition of dye can be eliminated from the process steps, thereby producing a polymer that is "natural" or undyed.

EXAMPLE 5

Dry Blending

Once the lactide/glycolide and poly(p-dioxanone) polymers have been produced by the above described methods, appropriate amounts of these components, in divided form (ground) were combined in a dry blend. These dry blends are produced on a weight basis, depending on the particular application and surgical need. In the present example, poly (p-dioxanone) at 20 weight percent and a lactide/glycolide copolymer at 80 weight percent, were dry blended.

In a clean 3-cubic foot Patterson-Kelley dryer, 36.0 kg of granules of the 85/15 molar lactide/glycolide copolymer of EXAMPLE 2 were weighed and added to the dryer. In the same 3-cubic foot dryer, 9.0 kg of poly(p-dioxanone) polymer granules of EXAMPLE 4 were weighed and added to the dryer. The dryer was closed, and the vessel pressure was reduced to less than 200 MTorr. The rotation was started at 7.5 RPM and continued for a minimum period of one hour. The dry blend was then discharged into portable vacuum storage containers, and these containers were placed under vacuum, until ready for the next step.

For the purpose of this invention, blends of this type can be produced in a similar manner with different compositions. Other inventive compositions that were made are summarized in Table I. Additionally, some blends of the prior art, specifically the Smith blends, were made for comparative sake. Three blends that were made contained 30 weight percent poly(p-dioxanone) and 70 weight percent of a lactide/glycolide copolymer possessing 80, 85 and 90 mol percent polymerized L(−)-lactide, respectively. Again, for some demanding situations, these blends containing greater than about 24 weight percent of poly(p-dioxanone) are too soft.

EXAMPLE 6

Melt Blending

Once the dry blends have been produced and have been vacuum conditioned for at least three days, the melt-blending step can begin. A ZSK-30 twin-screw extruder was fitted with screws designed for melt blending utilizing dual vacuum ports for purposes of volatilizing residual monomer. The screw design contained several different types of elements, including conveying, compression, mixing and sealing elements. The extruder was fitted with a three-hole die plate, and a chilled water bath with water temperature set between 40 and 70° F. was placed near the extruder outlet. A strand pelletizer and pellet classifier was placed at the end of the water bath. The extruder temperature zones were heated to a temperature of 160 to 180° C., and the vacuum cold traps were set to −20° C. The pre-conditioned dry blend granules were removed from vacuum and placed in a twin-screw feed hopper under nitrogen purge. The extruder screws were set to a speed of 175-225 RPM, and the feeder was turned on, allowing the dry blend to be fed into the extruder.

The polymer melt blend was allowed to purge through the extruder until the feed was consistent, at which point the vacuum was applied to the two vacuum ports. The polymer blend extrudate strands were fed through the water bath and into the strand pelletizer. The pelletizer cut the strands into appropriate sized pellets; it was found that pellets with a diameter of 1 mm and an approximate length of 3 mm suffice. The pellets were then fed into the classifier. The classifier separated larger and smaller pellets from the desired size, usually a weight of about 10-15 mg per pellet. This process continued until the entire polymer dry blend was melt blended in the extruder, and formed into substantially uniform pellets. Samples were taken throughout the extrusion process and were measured for polymer characteristics such as inherent viscosity, molecular weight and composition. Once the melt-blending process was completed, the pelletized polymer was placed in polyethylene bags, weighed, and stored in a freezer below −20° C. to await devolitilization of residual monomer.

The polymer melt-blend was placed into a 3-cubic foot Patterson-Kelley dryer, which was placed under vacuum. The dryer was closed and the pressure was reduced to less than 200 mTorr. Once the pressure was below 200 mTorr, dryer rotation was activated at a rotational speed of 10 RPM with no heat for 6 hours. After the 6 hour period, the oil temperature was set to 85° C. at a heat up rate of 120° C. per hour. The oil temperature was maintained at 85° C. for a period of 12 hours. At the end of this heating period, the batch was allowed to cool for a period of at least 4 hours, while maintaining rotation and vacuum. The polymer melt-blend pellets were discharged from the dryer by pressurizing the vessel with nitrogen, opening the discharge valve, and allowing the polymer pellets to descend into waiting vessels for long term storage. The storage vessels were air tight and outfitted with valves allowing for evacuation so that the resin was storage under vacuum. The resin was characterized.

The dry-blend of EXAMPLE 5 was melt-blended by the above described process. The resultant melt blend exhibited an inherent viscosity of 1.70 dL/g, as measured in hexafluoroisopropanol at 25° C. and at a concentration of 0.10 g/dL. Gel permeation chromatography analysis showed a weight average molecular weight of approximately 88,000 Daltons. Differential scanning calorimetry revealed two glass transition temperatures of about −15° C. and 55° C., and two melting transition temperatures at about 105 and 150° C. Nuclear magnetic resonance analysis confirmed that the resin was a blend of poly(p-dioxanone) and 85/15 (mol percent) lactide/glycolide copolymer, with a composition of approximately 64 percent polymerized lactide, 24 percent poly(p-dioxanone), and 11 percent polymerized glycolide, as measured on a molar basis. The total residual monomer content was less than 2 percent. X-ray diffraction analysis showed a crystallinity level of approximately 40 percent.

As mentioned previously in EXAMPLE 5, blends of various compositions comprising poly(p-dioxanone), polylactide homopolymers, and lactide-rich lactide/glycolide co-polymers were produced by the above described method. For the purposes of this invention, the polymers and melt-blends outlined below in Table I were produced using these methods. The polymer of EXAMPLES 1 and the melt blends of EXAMPLE 6 were injection molded into the surgical articles described in EXAMPLE 7, and were analyzed for their physical, biological and chemical characteristics.

TABLE I

Melt Blends of Poly (p-dioxanone) and a Lactide-Rich, Lactide/Glycolide (Co)Polymer

| EXAMPLE | Blend Composition Based on Weight Percent Poly(p-dioxanone)/ L/G Copolymer | Weight Percent Poly(p-dioxanone) | Mol Percent Lactide in the L/G Copolymer |
|---|---|---|---|
| 6A | 0% Poly(p-dioxanone)/ 100% PLA | 0.0 | 100.0 |
| 6B | 5% Poly(p-dioxanone)/ 95% PLA | 5.0 | 100.0 |
| 6C | 7.5% Poly(p-dioxanone)/ 92.5% PLA | 7.5 | 100.0 |
| 6D | 9% Poly(p-dioxanone)/ 91% PLA | 9.0 | 100.0 |
| 6H | 9% Poly(p-dioxanone)/ 91% 90/10 PLA/PGA | 9.0 | 90.0 |
| 6E | 10% Poly(p-dioxanone)/ 90% PLA | 10.0 | 100.0 |
| 6L | 10% Poly(p-dioxanone)/ 90% 85/15 PLA/PGA | 10.0 | 85.0 |
| 6J | 12% Poly(p-dioxanone)/ 88% 90/10 PLA/PGA | 12.0 | 90.0 |
| 6P | 13% Poly(p-dioxanone)/ 87% 80/20 PLA/PGA | 13.0 | 80.0 |
| 6K | 15% Poly(p-dioxanone)/ 85% 90/10 PLA/PGA | 15.0 | 90.0 |
| 6M | 15% Poly(p-dioxanone)/ 85% 85/15 PLA/PGA | 15.0 | 85.0 |
| 6S | 15% Poly(p-dioxanone)/ 85% 75/25 PLA/PGA | 15.0 | 75.0 |
| 6Q | 17% poly (p-dioxanone)/ 83% 80/20 PLA/PGA | 17.0 | 80.0 |
| 6T | 17.5% Poly(p-dioxanone)/ 82.5% 75/25 PLA/PGA | 17.5 | 75.0 |
| 6G | 20% Poly(p-dioxanone)/ 80% 95/5 PLA/PGA | 20.0 | 95.0 |
| 6N | 20% Poly(p-dioxanone)/ 80% 85/15 PLA/PGA | 20.0 | 85.0 |
| 6R | 20% Poly(p-dioxanone)/ 80% 80/20 PLA/PGA | 20.0 | 80.0 |
| 6W | 20% Poly(p-dioxanone)/ 80% 75/25 PLA/PGA | 20.0 | 75.0 |
| 6F | 24% Poly(p-dioxanone)/ 76% PLA | 24.0 | 100.0 |
| 6X | 24% Poly(p-dioxanone)/ 76% 75/25 PLA/PGA | 24.0 | 75.0 |

EXAMPLE 7

Test Article Description

The article chosen for evaluation was a 5 mm laparoscopic device for hernia repair; it was in the form of a staple or strap with legs and tissue holding means to the end of the legs. The device is illustrated in FIG. 2. The article was geometrically complex and was sterilized using conventional ethylene oxide sterilization processes after undergoing an annealing process. The device was used to fixate prosthetic mesh to soft tissue in both laparoscopic and open procedures.

EXAMPLE 8

Injection Molding

Injection molding is a process well known in the plastic industry. It is designed to produce parts of various shapes and sizes by melting the plastic, mixing and then injecting the molten resin into a suitably shaped mold. After the resin is solidified, the part is generally ejected from the mold and the process continued.

For the purposes of this invention, a conventional 30-ton electrically controlled injection molding machine was used. The polymer of EXAMPLE 1 and the polymer blends of EXAMPLE 6 were processed in the following general manner. The polymer and polymer blends were fed by gravity from a hopper, under nitrogen purge, into a heated barrel. The polymer was moved forward in the barrel by the screw-type plunger into a heated chamber. As the screw advanced forward, the molten polymer and polymer blends were forced through a nozzle that rests against a mold, allowing the polymer and polymer blends to enter a specially designed mold cavity, through a gate and runner system. The blend was formed into the part in the mold cavity, and allowed to cool at a given temperature for a period of time. It was then removed from the mold, or ejected, and separated from the gate and runner. The injection molding cycle consisted of the entire series of events during the process. It began when the mold closed, and was followed by the injection of the polymer and polymer blends into the mold cavity. Once the cavity was filled, hold pressure was maintained to compensate for material shrinkage. Next, the screw-plunger turned, feeding the next "shot" to the front of the screw. The screw retracted as the next "shot" was prepared. The part was cooled in the mold to sufficient temperature, and the mold opened and the part was ejected. The closing and ejection times lasted from a fraction of a second to a few seconds. Cooling times were based on a number of factors, including part size and material composition.

EXAMPLE 9

Annealing the Molded Part

Once the articles of EXAMPLE 8 were injection molded, they were then subjected to an annealing cycle to mature the polymer morphology. As noted earlier, this often increases the level of crystallinity in the part. The articles in EXAMPLE 8 were annealed using an annealing fixture that supported the parts from distortion within the horizontal plane of the part. Although this annealing fixture is intended to aid in the resistance of distortion at elevated temperatures during annealing, it will not prevent dimensionally unstable parts from warping.

The annealing cycle used for the articles in EXAMPLE 8 was composed of three steps: 60° C. for 8 hours, 70° C. for 4 hours, and then 80° C. for 4 hours. The purpose of the 60° C. step is to further crystallize the poly(p-dioxanone) phase in the blend before reaching the crystallization temperatures for the poly(lactide-co-glycolide) phase. The 70° C. step begins to crystallize the poly(lactide-co-glycolide) phase before reaching the last step in the cycle. Finally, the 80° C. step further crystallizes the poly(lactide-co-glycolide) phase.

It should be noted that for a given device and given composition annealing conditions may be found that optimize certain important performance characteristics. These advantageous annealing conditions can be developed through experimentation, changing the annealing temperature and annealing duration, and measuring the response.

EXAMPLE 10

Analytical Characterization of Molded Parts

In general, the molded parts were characterized for chemical composition by Nuclear Magnetic Resonance (NMR); for molecular weight by inherent viscosity in hexafluoroisopropanol at 0.1 g/dL at 25° C., and/or gel permeation chromatography (GPC); for morphology by X-ray diffraction, differential scanning calorimetry (DSC), and chemical etching. Analysis was performed on parts prior to annealing, after annealing, and often after EO sterilization.

Crystallinity levels of selected lots of the annealed injection molded articles can be found in the table below.

TABLE II

Crystallinity Levels of Selected Lots of the Annealed Injection Molded articles

| Poly(p-dioxanone) Weight Percent in the Blend | Molar Percent of Glycolide Content in the Lactide/Glycolide Copolymer | Percent Crystallinity Level as Measured by X-Ray Diffraction |
| --- | --- | --- |
| 20 | 10 | 45.0 |
| 20 | 10 | 45.9 |
| 20 | 12 | 46.4 |
| 20 | 15 | 38.4 |
| 20 | 15 | 39.9 |
| 20 | 15 | 38.2 |
| 20 | 15 | 42.6 |
| 20 | 20 | 38.9 |
| 30 | 15 | 36.3 |
| 30 | 20 | 45.6 |

EXAMPLE 11

In Vitro Testing; Mechanical Properties

Selected lots of the annealed injection molded articles of EXAMPLE 9 were tested for their mechanical properties using an INSTRON tensile testing machine, Model 5544 fitted with an appropriate load cell. The articles were placed in a fixture designed to grip the barbed legs on one end and the crown on the other. The force-to-break was recorded as "Zero-Day Breaking Strength".

EXAMPLE 12

In Vitro Testing; BSR Testing

Figure 4:
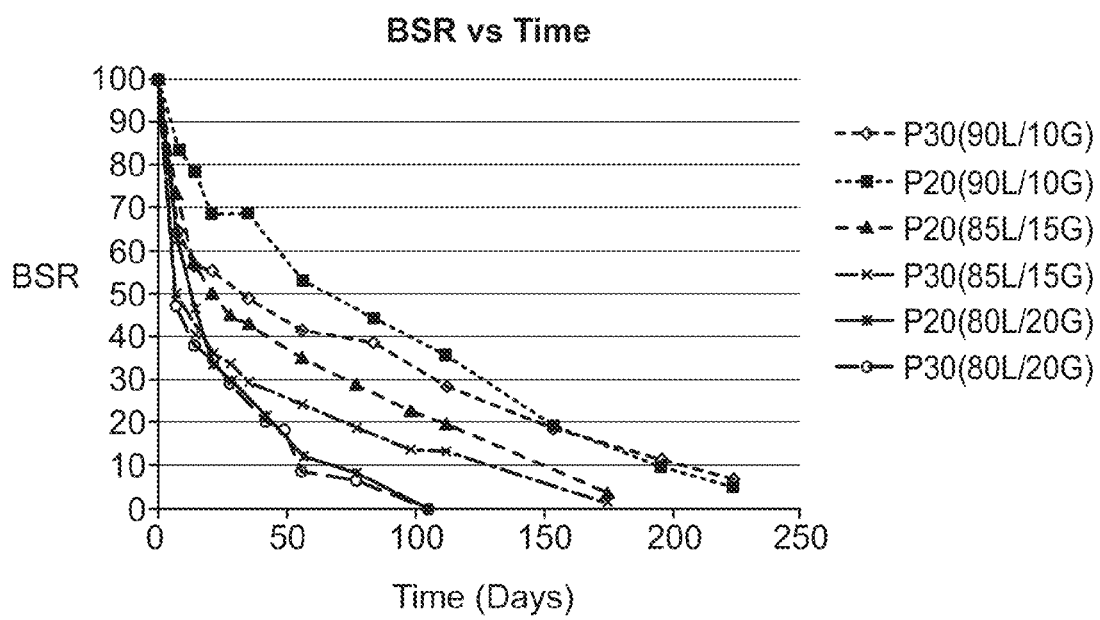
FIG. 4 is a graph showing the effects of compositional changes of the injection molded device, as related to breaking strength retention or BSR, after being subjected to in-vitro testing.

Selected lots of the annealed injection molded articles of EXAMPLE 9 were placed in containers filled with a suitable amount of phosphate buffer at pH 7.27. The containers were then incubated at 37° C. and a representative sample size, typically ten, was retrieved periodically for mechanical testing. The incubated articles were tested for their mechanical properties using an INSTRON tensile testing machine in a fashion similar to the method of EXAMPLE 11. The force-to-break was recorded as "Breaking Strength". The ratio of "Breaking Strength" to "Zero-Day Breaking Strength" was calculated and reported as "Breaking Strength Retention" for each time period. The test results are graphically presented in FIG. 4. FIG. 4 is a graph showing the effects of compositional changes of the injection molded device, as related to breaking strength retention or BSR, after being subjected to in-vitro testing.

EXAMPLE 13

Penetration

The test articles of EXAMPLE 9N were tested for their ability to penetrate bodily tissue and affix surgical mesh. Using an INSTRON machine, the force needed to affix a commercially available surgical mesh to porcine big belly was measured. The penetration test utilized custom top and bottom fixtures. The top fixture was a seating fork to push the tack through the mesh, while the bottom fixture was a clamp to hold the porcine belly in place.

The test articles of Example 9N were found to function appropriately. That is to say that they displayed appropriate tip sharpness, dimensional stability, and had adequate stiffness and column strength. Depending on the functional need of the article, this stiffness may be increased by decreasing the level of poly(p-dioxanone), such as for orthopedic applications. Likewise, the stiffness may be decreased by increasing the level of poly(p-dioxanone), such as for soft tissue applications.

EXAMPLE 14

Holding Strength

The ability to hold the surgical mesh to bodily tissue is an important function, especially during the critical wound healing period. The affixed surgical mesh was subjected to mechanical forces to determine the force required to disengage the mesh from the tissue; this force is called "Holding Strength". More specifically, surgical mesh was affixed to porcine belly by inserting three articles from EXAMPLE 9N along one side of the mesh. The mesh was then grasped with clamps attached to a forced gauge and pulled in a shear direction (parallel to the plane of the tissue) until the mesh disengaged from the tissue. The maximum force was recorded as the "Holding Strength". Articles of EXAMPLE 9N generated holding force values of about 10 to 11 pounds. Depending of the medical application, the holding strength requirement will vary and the composition of the article utilized can be tailored to meet that requirement.

Holding strength data for articles made from blends of various weight average molecular weights at the 20 weight percent poly(p-dioxanone)/80 weight percent 85/15 poly(L (−)-lactide-co-glycolide) composition was obtained. The data is provided in Table III below:

TABLE III

Holding Strength Data at Various Molecular Weights

| Weight Average Molecular Weight (Da) | Holding Strength (lbs) |
|---|---|
| 91,200 | 11.06 |
| 85,100 | 10.34 |
| 74,200 | 10.34 |
| 66,600 | 10.95 |
| 58,000 | 10.16 |
| 53,400 | 10.80 |

EXAMPLE 15

Dimensional Stability

The unannealed articles of EXAMPLE 8N were subject to x-ray diffraction analysis, and displayed crystallinity levels of about 11 to 12 percent overall. The majority of the crystallinity was assigned by x-ray diffraction techniques to the poly(p-dioxanone) phase. Once annealed, the molded parts had superior dimensional stability. The articles of EXAMPLE 9 exhibited greater crystallinity levels than their EXAMPLE 8 counterparts. Indeed, the annealed articles of EXAMPLE 9N were also analyzed by x-ray diffraction and showed higher crystallinity levels of about 38 to 41 percent.

The molded articles of EXAMPLE 9 were tested for dimensional stability. The dimensions of the molded articles were measured prior to annealing and after annealing; additionally photographic images were taken. Although it is not expected to have dimensions match exactly, it is clear that unacceptable levels of distortion exist. In some cases, excessive distortion results in diminished functionality.

The test articles of EXAMPLE 9 are geometrically complex and have a number of critical dimensions. For instance, if the legs of the molded article distort excessively, the ability of the device to penetrate and hold tissue will be reduced. Likewise, if the barbs of the molded article were to shrink significantly, functionality would be reduced because of diminished ability to hold tissue. Every design will have its own critical dimensions. It is believed that the design of EXAMPLE 7 is representative of a demanding device regarding dimensional stability; this is felt in part because of geometric complexity. Additionally, the fine part size will tend to increase molecular orientation during injection molding leading to an increased driving force for distortion of the ejected part at elevated temperatures as seen in annealing, and/or sterilization, and/or storage.

Parts were evaluated and characterized in a "pass/fail" manner. Disposition of the molded articles were based on gross warping effects, of which an article is considered to have passed if excessive distortion is not evident. Likewise, if excessive distortion is evident, the part is said to have failed. Inherently, all injection molded articles have some degree of residual stress after molding, so parts that display tolerable levels of distortion are said to have passed the dimensional stability test.

For the articles of EXAMPLE 9, the tip-to-tip distance is a critical dimension; see FIG. 3. FIG. 3 is a drawing of the device of FIG. 2 showing the critical dimensions of said device. These dimensions, if changed by lack of dimensional stability, can lead to poor performance and or failure of the device. A tip-to-tip distance of less than to 0.115 inches for the articles of EXAMPLE 9 were said to be acceptable, while a tip-to-top distance greater than or equal to 0.115 inches were said to be unacceptable and denoted as "failure mode one" or "fm1". Likewise, the length of the barb members from EXAMPLE 9 were also considered critical dimensions. A barb length of less than or equal to 0.136 inches were considered unacceptable and denoted as "failure mode 2" or "fm2"

The photographic images and dimensions were captured using a Keyence digital microscope, model VHX-600, with a magnification of 20×. The test results are shown in Table IV.

TABLE IV

Dimensional Stability Results on Injection Molded Articles of EXAMPLES 8 and 9 made from the Lactide-Rich Lactide/Glycolide (Co)Polymer with Poly(p-dioxanone) Melt Blends of EXAMPLE 6

| Molded Device EXAMPLE No.* | Before Annealing FIG. No. | After Annealing FIG. No. | Dimensional Stability Grade/ Reason For Failure** |
|---|---|---|---|
| 8 and 9 A (0, 100) | | | Failed: fm1, fm2 |
| 8 and 9 B (5, 100) | | | Failed: fm1 |
| 8 and 9 C (7.5, 100) | 6a | 6b | Failed: fm1 |
| 8 and 9 D (9, 100) | 7a | 7b | Pass |
| 8 and 9 E (10, 100) | | | Pass |
| 8 and 9 F (24, 100) | | | Pass |
| 8 and 9 G (20, 95) | | | Pass |
| 8 and 9 H (9, 90) | | | Failed: fm1, fm2 |
| 8 and 9 J (12, 90) | | | Pass |
| 8 and 9 K (15, 90) | | | Pass |
| 8 and 9 L (10, 85) | | | Failed: fm1 |
| 8 and 9 M (15, 85) | | | Pass |
| 8 and 9 N (20, 85) | 8a | 8b | Pass |
| 8 and 9 P (13, 80) | | | Failed: fm2 |
| 8 and 9 Q (17, 80) | | | Pass |
| 8 and 9 R (20, 80) | | | Pass |
| 8 and 9 S (15, 75) | 9a | 9b | Failed: fm1 |
| 8 and 9 T (17.5, 75) | 10a | 10b | Pass |
| 8 and 9 W (20, 75) | | | Pass |
| 8 and 9 X (24, 75) | 11a | 11b | Pass |

Figure 6A:
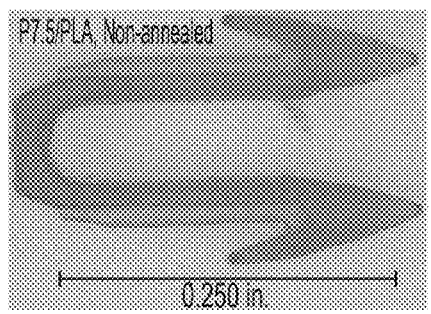
FIG. 6a is a photograph of an injection molded tack of EXAMPLE 8C (i.e., prior to annealing) made from the polymer composition of EXAMPLE 6C that provided injection molded tacks exhibiting unacceptable warping after annealing.
Figure 6B:
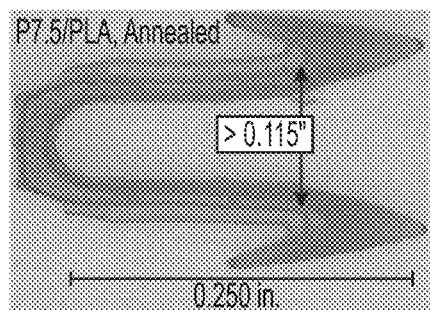
FIG. 6b is a photograph of an injection molded tack of EXAMPLE 9C (similar to the tack of FIG. 6a, but after annealing) made from the polymer composition of EXAMPLE 6C that provided injection molded tacks exhibiting unacceptable warping after annealing.

*EXAMPLE 8 refers to the molded articles prior to annealing, while EXAMPLE 9 is after annealing
**Key for Mode of Failure: fm1 = Increase in tip-to-tip distance; fm2 = Shrinkage of one or both barbs FIG. 6a is a photograph of an injection molded tack of EXAMPLE 8C (i.e., prior to annealing) made from the polymer composition of EXAMPLE 6C that provided injection molded tacks exhibiting unacceptable warping after annealing. FIG. 6b is a photograph of an injection molded tack of EXAMPLE 9C (similar to the tack of FIG. 6a, but after annealing) made from the polymer composition of EXAMPLE 6C that provided injection molded tacks exhibiting unacceptable warping after annealing.

Figure 7A:
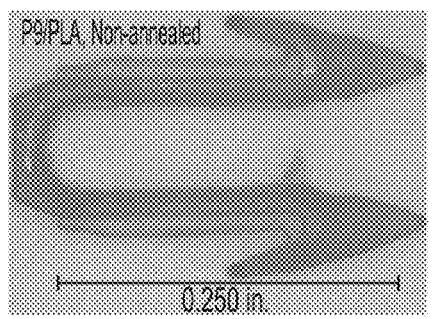
FIG. 7a is a photograph of an injection molded tack of EXAMPLE 8D (i.e., prior to annealing) made from the polymer composition of EXAMPLE 6D that provided injection molded tacks that exhibit superior dimensional stability and an acceptable level of warping after annealing.
Figure 7B:
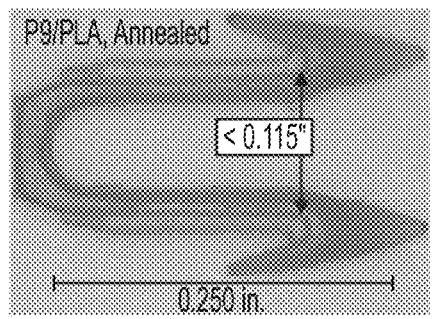
FIG. 7b is a photograph of an injection molded tack of EXAMPLE 9D (similar to the tack of FIG. 7a, but after annealing) made from the polymer composition of EXAMPLE 6D that provides injection molded tacks that exhibit superior dimensional stability and an acceptable level of warping after annealing.

FIG. 7a is a photograph of an injection molded tack of EXAMPLE 8D (i.e., prior to annealing) made from the polymer composition of EXAMPLE 6D that provided injection molded tacks that exhibit superior dimensional stability and an acceptable level of warping after annealing. FIG. 7b is a photograph of an injection molded tack of EXAMPLE 9D (similar to the tack of FIG. 7a, but after annealing) made from the polymer composition of EXAMPLE 6D that provided injection molded tacks that exhibited superior dimensional stability and an acceptable level of warping after annealing.

Figure 8A:
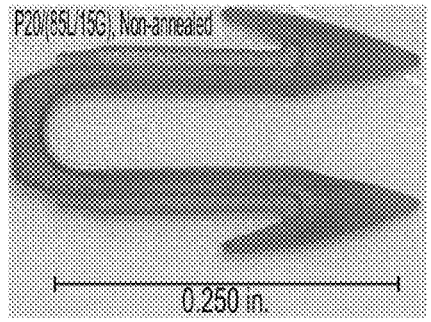
FIG. 8a is a photograph of an injection molded tack of EXAMPLE 8N (i.e., prior to annealing) made from the polymer composition of EXAMPLE 6N that provided injection molded tacks that exhibit superior dimensional stability and an acceptable level of warping after annealing.
Figure 8B:
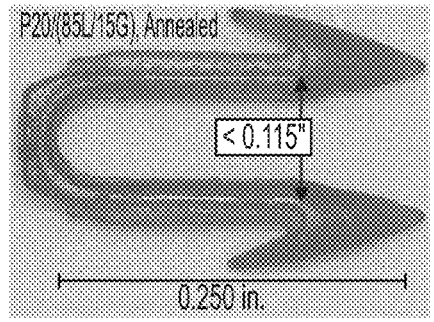
FIG. 8b is a photograph of an injection molded tack of EXAMPLE 9N (similar to the tack of FIG. 8a, but after annealing) made from the polymer composition of EXAMPLE 6N that provided injection molded articles that exhibit superior dimensional stability and an acceptable level of warping after annealing.

FIG. 8a is a photograph of an injection molded tack of EXAMPLE 8N (i.e., prior to annealing) made from the polymer composition of EXAMPLE 6N that provided injection molded tacks that exhibited superior dimensional stability and an acceptable level of warping after annealing. FIG. 8b is a photograph of an injection molded tack of EXAMPLE 9N (similar to the tack of FIG. 8a, but after annealing) made from the polymer composition of EXAMPLE 6N that provided injection molded articles that exhibited superior dimensional stability and an acceptable level of warping after annealing.

Figure 9A:
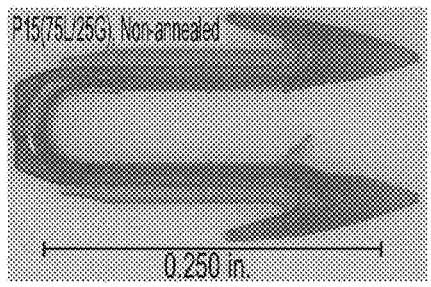
FIG. 9a is a photograph of an injection molded tack of EXAMPLE 8S (i.e., prior to annealing) made from the polymer composition of EXAMPLE 6S that provided injection molded tacks that exhibit unacceptable warping after annealing.
Figure 9B:
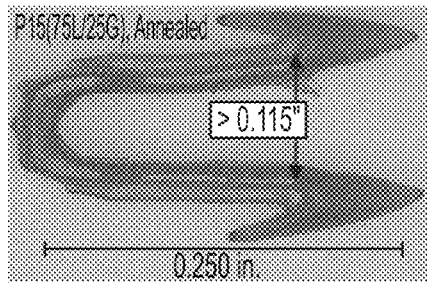
FIG. 9b is a photograph of an injection molded tack of EXAMPLE 9S (similar to the tack of FIG. 9a, but after annealing) made from the polymer composition of EXAMPLE 6S, that provided injection molded tacks that exhibit unacceptable warping after annealing.

FIG. 9a is a photograph of an injection molded tack of EXAMPLE 8S (i.e., prior to annealing) made from the polymer composition of EXAMPLE 6S that provided injection molded tacks that exhibited unacceptable warping after annealing. FIG. 9b is a photograph of an injection molded tack of EXAMPLE 9S (similar to the tack of FIG. 9a, but after annealing) made from the polymer composition of EXAMPLE 6S, that provided injection molded tacks that exhibited unacceptable warping after annealing.

Figure 10A:
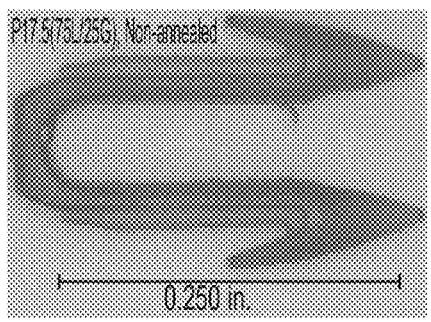
FIG. 10a is a photograph of an injection molded tack of EXAMPLE 8T (i.e., prior to annealing) made from the polymer composition of EXAMPLE 6T that provided injection molded tacks that exhibit superior dimensional stability and an acceptable level of warping after annealing.
Figure 10B:
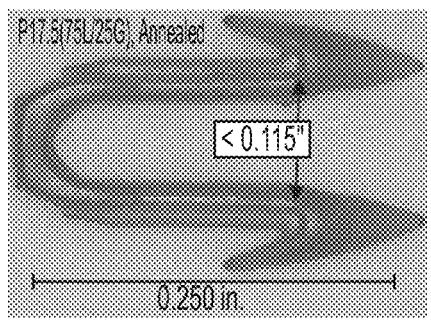
FIG. 10b is a photograph of an injection molded tack of EXAMPLE 9T (similar to the tack of FIG. 10a, but after annealing) made from the polymer composition of EXAMPLE 6T that provided injection molded tacks that exhibit superior dimensional stability and an acceptable level of warping after annealing.

FIG. 10a is a photograph of an injection molded tack of EXAMPLE 8T (i.e., prior to annealing) made from the polymer composition of EXAMPLE 6T that provided injection molded tacks that exhibited superior dimensional stability and an acceptable level of warping after annealing. FIG. 10b is a photograph of an injection molded tack of EXAMPLE 9T (similar to the tack of FIG. 10a, but after annealing) made from the polymer composition of EXAMPLE 6T that provided injection molded tacks that exhibited superior dimensional stability and an acceptable level of warping after annealing.

Figure 11A:
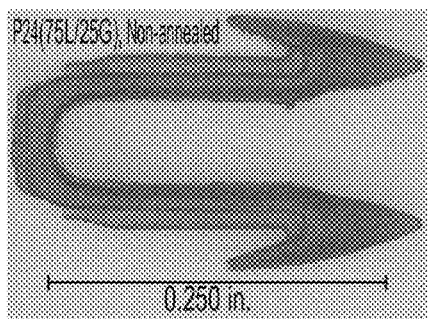
FIG. 11a is a photograph of an injection molded tack of EXAMPLE 8X (i.e., prior to annealing) made from the polymer composition of EXAMPLE 6X that provided injection molded tacks that exhibit superior dimensional stability and an acceptable level of warping after annealing.
Figure 11B:
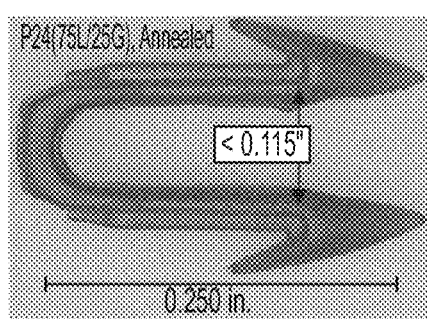
FIG. 11b is a photograph of an injection molded tack of EXAMPLE 9X (similar to the tack of FIG. 11a, but after annealing) made from the polymer composition of EXAMPLE 6X that provided injection molded tacks that exhibit superior dimensional stability and an acceptable level of warping after annealing.

FIG. 11a is a photograph of an injection molded tack of EXAMPLE 8X (i.e., prior to annealing) made from the polymer composition of EXAMPLE 6X that provided injection molded tacks that exhibited superior dimensional stability and an acceptable level of warping after annealing. FIG. 11b is a photograph of an injection molded tack of EXAMPLE 9X (similar to the tack of FIG. 11a, but after annealing) made from the polymer composition of EXAMPLE 6X that provided injection molded tacks that exhibited superior dimensional stability and an acceptable level of warping after annealing.

EXAMPLE 16

Absorption Profile

The articles of the present invention are absorbable in bodily tissue. In general, the greater the amount of glycolide in the lactide-rich poly(lactide-co-glycolide) copolymer, the faster the article will absorb. Additionally, the greater the amount of poly(p-dioxanone) in the polymer blend, the faster the article will absorb.

Annealed injection molded articles substantially similar in design to FIG. 2 made from polymer blends of lactide-rich poly(lactide-co-glycolide) and poly(p-dioxanone) were tested for hydrolysis time at a pH of 7.27 and a temperature of 70° C. The data in Table V summarizes the results of this accelerated hydrolysis test.

TABLE V

Accelerated Hydrolysis Values

| Mol Percent of Polymerized Lactide in the Lactide-Based (Co)Polymer | Weight Percent Poly(p-dioxanone) Polymer in the Blend | Time for Complete Hydrolysis (Hours) |
|---|---|---|
| 90 | 20 | 360 |
| 85 | 30 | 260 |
| 80 | 20 | 220 |
| 80 | 30 | 200 |

EXAMPLE 17

Determination of Blend Morphology

A determination was made of the morphology of the minor component of the injection molded articles from the polymer blend of 20 weight percent poly(p-dioxanone) and 80 weight percent poly(lactide-co-glycolide), wherein the poly(lactide-co-lactide) is 85 mol percent lactide and 15 mol percent glycolide. The photomicrograph was obtained according to the following procedure: an injection molded device was cut into 8 small pieces to expose all internal structures; the small pieces were immersed in chloroform (5 ml) overnight to dissolve the poly(lactide-co-glycolide) component of the blend. The chloroform solution then was shaken to break the entangled fibrous structure; the solution then was passed through a polypropylene filter with a pore size of 0.3 μm; the filter was then rinsed with chloroform to remove any possible lactide/glycolide copolymer deposited on the filter; the poly (p-dioxanone) structures left on the filter surface then were studied with SEM.

FIG. 1 is an SEM photomicrograph of the collected poly (p-dioxanone) structures of the injection molded articles from the polymer blend of 20 weight percent poly(p-dioxanone) and 80 weight percent poly(lactide-co-glycolide), wherein the poly(lactide-co-lactide) is 85 mol percent lactide and 15 mol percent glycolide. The aspect ratio of the poly(p-dioxanone) phase is well above one indicating a high level of shear during the fabrication process which typically leads to high residual stress levels increasing the driving force for subsequent shrinkage and warpage.

EXAMPLE 18

Applicability of Inventive Blend for Medical Devices

It is to be understood that the blend of the present invention can be used to fabricate medical devices using various melt processing techniques. As shown in some of the above examples, injection molding is one of the techniques that is applicable. It is further understood that a variety of designs may be employed utilizing the inventive blends.

Figure 12:
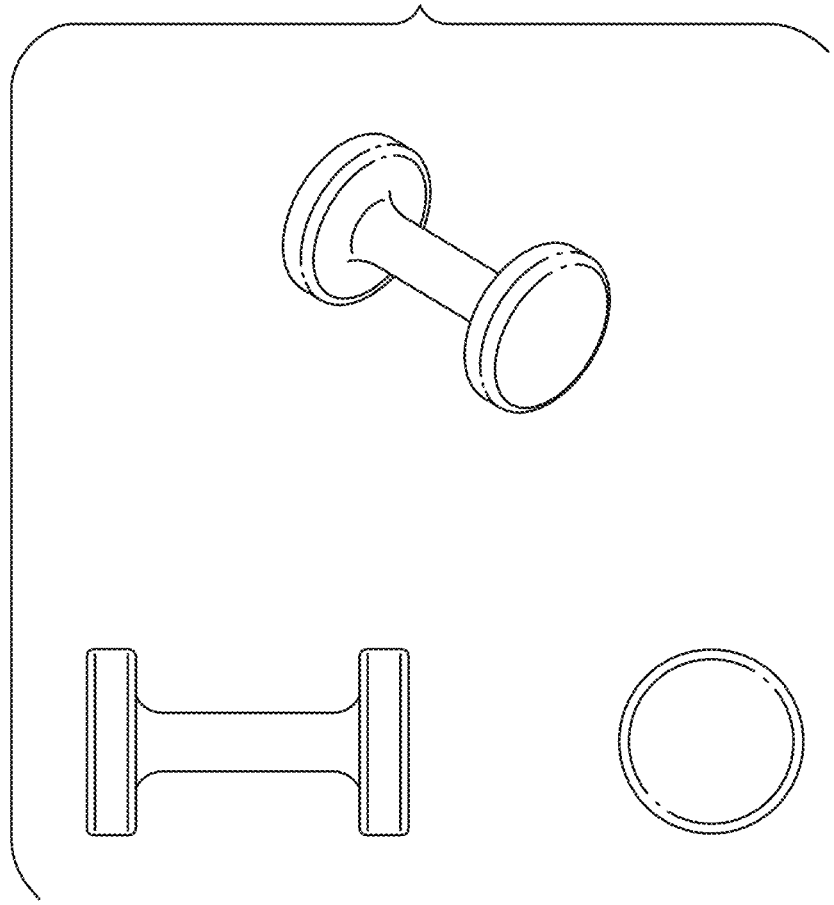
FIG. 12 is a drawing of a dumbbell test article.

One such device that was produced was in the form of a dumbbell 0.35 inches in length with substantially disk-like termini 0.20 inches in diameter and 0.05 inches in thickness. The connection between the two disks had a substantially circular cross-section, 0.062 inches in diameter. FIG. 12 provides engineering drawings of this dumbbell device. This design was injection molded using a 90/10 lactide/glycolide copolymer as a control and a polymer blend of the present invention, specifically a melt blend of 20 weight percent poly(p-dioxanone) and 80 weight percent 90/10 lactide/glycolide copolymer. The articles, so produced, were thermally annealed without restraint at 60, 70, and 80 C for 8, 4 and 4 hours, respectively. The devices molded from the 90/10 lactide/glycolide copolymer showed substantial shrinkage and warpage after this annealing process. The devices molded from the inventive blend were substantially free of shrinkage and warpage after annealing.

It is expected that the blends of the present invention would be useful in fabricating, via injection molding, a very wide array of devices including, but not limited to staples, pins, screws, plates, clips, anchors, tissue engineering scaffolds, and wound closure devices. In addition it is also expected that other processing methods might be employed to form useful articles using the present inventive blends. These processes include, but are not limited to, fiber extrusion, profile extrusion, film extrusion, tube extrusion, and blow molding. One skilled in the art could for instance cut or punch specific shapes to fabricate devices from sheet stock formed from extrusion methodologies. It will be evident to one skilled in the art to select an appropriate forming methodology.

EXAMPLE 19

Melt Blending During Fabrication of the Medical Device

As mentioned earlier, an alternate method of forming the melt blend of the present invention was to add the appropriately sized blend components directly to the hopper of the injection molding machine. The melt blending occurred within the confines of the injection molding machine's barrel producing acceptable parts as described in EXAMPLE 7.

EXAMPLE 20

Calculating the Minimum Weight Percent of Poly(p-Dioxanone) in the Invention

As stated previously, the minimum level of poly(p-dioxanone) was dependent on the molar amount of polymerized lactide present in the lactide-based polymer present in the blend and was calculated using the equation found below.

$$\text{Weight Percent Poly(p-dioxanone)} = (215.6212/\text{Mol Percent Polymerized Lactide})^{2.7027}$$

For example, when the composition of the lactide-co-glycolide copolymer was 82/8 (on a mol basis), the minimum weight percent of poly(p-dioxanone) in the blend was calculated to be 10 percent and the maximum amount was approximately 24. Likewise, if the composition of the lactide-co-glycolide copolymer was 86/14 (on a mol basis), the minimum weight percent of poly(p-dioxanone) in the blend was calculated to be 12 percent and the maximum amount was approximately 24. Table VI contains a chart of the range of poly(p-dioxanone), expressed as minimum and maximum weight percent, in the blend of the subject invention.

TABLE VI

Inventive Blend Compositions of Lactide-Rich, Lactide/Glycolide (Co)Polymer with Poly(p-dioxanone)

| Mol Percent of Polymerized Lactide in the Lactide-Based (Co)Polymer | Minimum Weight Percent Poly(p-dioxanone) Polymer in the Blend | Maximum Weight Percent Poly(p-dioxanone) Polymer in the Blend |
|---|---|---|
| 100 | 8.0 | Approximately 24 |
| 99 | 8.2 | Approximately 24 |
| 98 | 8.4 | Approximately 24 |
| 97 | 8.7 | Approximately 24 |
| 96 | 8.9 | Approximately 24 |
| 95 | 9.2 | Approximately 24 |
| 94 | 9.4 | Approximately 24 |
| 93 | 9.7 | Approximately 24 |
| 92 | 10.0 | Approximately 24 |
| 91 | 10.3 | Approximately 24 |
| 90 | 10.6 | Approximately 24 |
| 89 | 10.9 | Approximately 24 |
| 88 | 11.3 | Approximately 24 |
| 87 | 11.6 | Approximately 24 |
| 86 | 12.0 | Approximately 24 |
| 85 | 12.4 | Approximately 24 |
| 84 | 12.8 | Approximately 24 |
| 83 | 13.2 | Approximately 24 |
| 82 | 13.6 | Approximately 24 |
| 81 | 14.1 | Approximately 24 |
| 80 | 14.6 | Approximately 24 |
| 79 | 15.1 | Approximately 24 |
| 78 | 15.6 | Approximately 24 |
| 77 | 16.2 | Approximately 24 |
| 76 | 16.7 | Approximately 24 |
| 75 | 17.4 | Approximately 24 |
| 74 | 18.0 | Approximately 24 |
| 73 | 18.7 | Approximately 24 |
| 72 | 19.4 | Approximately 24 |
| 71 | 20.1 | Approximately 24 |
| 70 | 20.9 | Approximately 24 |

Figure 5:
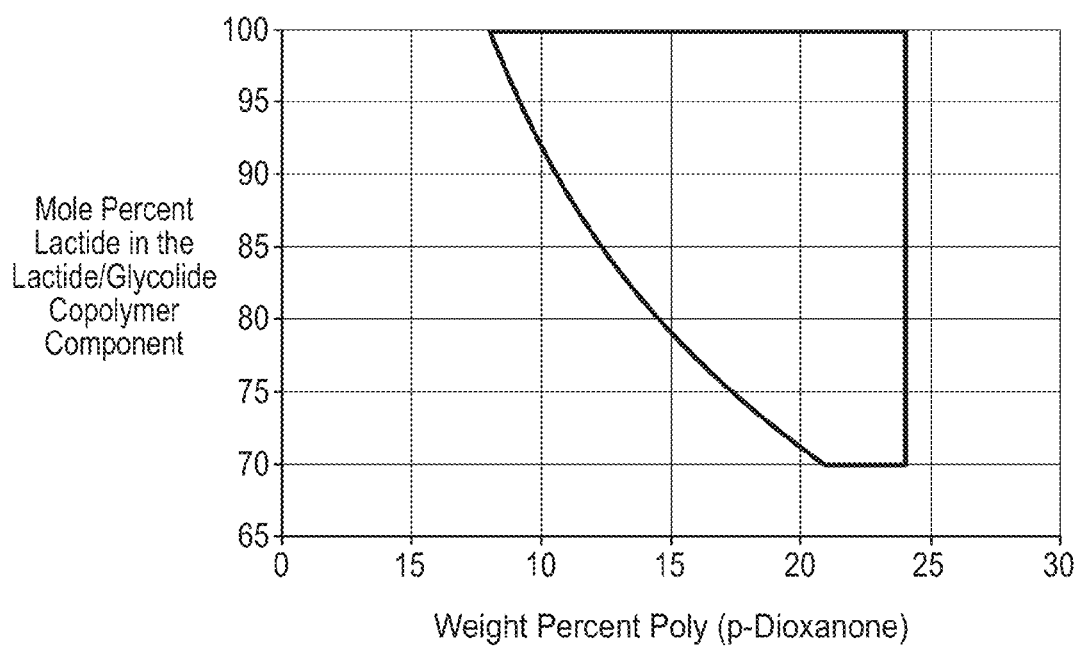
FIG. 5 is a graph of mol percent polymerized lactide in the lactide/glycolide copolymer component versus weight percent of poly(p-dioxanone); the area bounded by the curves contains the novel polymer compositions of the present invention.

FIG. 5 is a graph of mol percent lactide in the lactide/glycolide copolymer component versus weight percent of poly(p-dioxanone); the area bounded by the curves shows the novel polymer compositions of the present invention.

Although this invention has been shown and described with respect to detailed embodiments thereof, it will be understood by those skilled in the art that various changes in form and detail thereof may be made without departing from the spirit and scope of the claimed invention.

We claim:

1. A method of manufacturing a bioabsorbable medical device, comprising the steps of:
   processing a bioabsorbable polymer blend comprising 78 weight percent to 82 weight percent of a first bioabsorbable polymer and 18 weight percent to 22 weight percent of a second bioabsorbable polymer, the first bioabsorbable polymer comprising a lactide-rich polymer comprising 95 mol percent to 70 mol percent polymerized lactide and 5 mol percent to 30 mol percent polymerized glycolide, and the second bioabsorbable polymer comprising poly(p-dioxanone),
   wherein the maximum weight percent of poly(p-dioxanone) in the polymer blend is 22 weight percent and the minimum weight percent of poly(p-dioxanone) in the polymer blend depends upon the molar amount of polymerized lactide in the lactide-rich polymer and is calculated by the expression:

$$\text{Minimum Weight Percent Poly(p-dioxanone)} = (215.6212/\text{Mol Percent Polymerized Lactide})^{2.7027}$$

and forming a bioabsorbable medical device from the polymer blend, wherein the polymer blend provides dimensional stability to the formed device.

2. The method of claim 1, wherein the lactide-rich polymer comprises about 80 mol percent to about 90 mol percent of polymerized lactide and from about 10 mol percent to about 20 mol percent of polymerized glycolide.

3. The method of claim 2, wherein the lactide-rich polymer comprises about 83 mol percent to about 87 mol percent of polymerized lactide and from about 13 mol percent to about 17 mol percent of polymerized glycolide.

4. The method of claim 1, wherein the polymer blend has an inherent viscosity of at least about 0.8 dL/g as measured in hexafluoroisopropanol at 25 degrees centigrade at a concentration of 0.1 g/dL.

5. The method of claim 1, wherein the first bioabsorbable polymer has an inherent viscosity of at least about 0.8 dL/g as measured in hexafluoroisopropanol at 25 degrees centigrade at a concentration of 0.1 g/dL.

6. The method of claim 1, wherein the second bioabsorbable polymer has an inherent viscosity of at least about 0.8 dL/g as measured in hexafluoroisopropanol at 25 degrees centigrade at a concentration of 0.1 g/dL.

7. The method of claim 1, wherein the polymer blend has a crystallinity of at least about 15 percent as measured by x-ray diffraction.

8. The method of claim 1, wherein the polymer blend additionally comprises an antimicrobial agent.

9. The method of claim 8, wherein the antimicrobial agent is a polychloro phenoxy phenol.

10. The method of claim 1, wherein the polymer blend additionally comprises a bioglass.

11. The method of claim 10, wherein the bioglass is selected from the group consisting of hydroxy apatite, tricalcium phosphate, carbonates, sulfate, oxides of calcium and magnesium.

12. The method of claim 1, wherein the polymer blend additionally comprises a therapeutic agent.

13. The method of claim 12, wherein the therapeutic agent is selected from the group consisting of antibiotics, antivirals, adhesion preventatives, contraceptives, and analgesics.

14. The method of claim 1, wherein the polymer blend further comprises an additional polymer.

15. The method of claim 14, wherein the additional polymer is selected from the group consisting of a synthetic absorbable polymer, and a natural absorbable polymer.

16. The method of claim 1, wherein the medical device is selected from the group consisting of staples, tacks, clips, sutures, tissue fixation devices, mesh fixation devices, anastomosis devices, suture and bone anchors, tissue and bone screws, prostheses, support structures, tissue augmentation devices, tissue ligating devices, patches, substrates, meshes, tissue engineering scaffolds, drug delivery devices, and stents.

17. The method of claim 16, wherein the medical device is a mesh fixation device which is selected from the group consisting of tacks and staples.

18. The method of claim 1, wherein the medical device is additionally exposed to a sterilization process.

19. The method of claim 1, wherein the aspect ratio of the second bioabsorbable polymer is greater than about 3.

20. The method of claim 19, wherein the aspect ratio of the second bioabsorbable polymer is greater than about 5.

21. The method of claim 20, wherein the aspect ratio of the second bioabsorbable polymer is greater than about 20.

22. The method of claim 1, wherein the medical device remains dimensionally stable when subjected to immersion in water at an elevated temperature.

23. The method of claim 1, wherein the medical device remains dimensionally stable when subjected to immersion in water at an elevated temperature of 49 degrees centigrade.

24. The method of claim 1, wherein the medical device remains dimensionally stable when subjected to immersion in water at an elevated temperature of 70 degrees centigrade.

25. The method of claim 1, wherein the polymer blend is formed by thermal processing.

26. The method of claim 25, wherein the thermal processing means is selected from the group consisting of polymerization, melt blending, and residual monomer removal by solvent extraction or devolatilization.

27. The method of claim 26, wherein the melt blending occurs directly in a process selected from the group consisting of injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion.

28. The method of claim 1, wherein the processing comprises one or more process steps selected from the group consisting of polymerization, pelletization, grinding, particle sizing, dry blending, melt blending, twin screw blending, single screw extrusion, co-extrusion, twin screw blending with simultaneous vented-screw vacuum devolatilization, residual monomer removal by solvent extraction, vacuum tumble drying, devolitilization, and resin annealing.

29. The method of claim 1, wherein the medical device is formed by a process selected from the group consisting of injection molding, compression molding, blow molding, blown film, thermoforming, film extrusion, fiber extrusion, sheet extrusion, profile extrusion, melt blown nonwoven extrusion, co-extrusion, tube extrusion, foaming, rotomolding, calendaring, and extrusion.

30. The method of claim 1, additionally comprising a step wherein the device is thermally annealed at a temperature of at least 45 degrees centigrade for at least one minute.

31. The method of claim 30, wherein the medical device is thermally annealed at a temperature of about 60 degrees centigrade for about 8 hours, followed by annealing at a temperature of about 70 degrees centigrade for about 4 hours, followed by annealing at a temperature of about 80 degrees centigrade for about 4 hours.

32. The method of claim 1, wherein the medical device additionally comprises a colorant.

33. The method of claim 32, wherein the colorant is selected from the group consisting of D&C Violet No. 2 and D&C Blue No. 6, at an amount ranging from about 0.01 weight percent to about 0.3 weight percent of the implanted portion of the device.

* * * * *